(12) United States Patent
Kamen

(10) Patent No.: US 7,999,674 B2
(45) Date of Patent: Aug. 16, 2011

(54) DEVICE AND METHOD FOR FOOD MANAGEMENT

(75) Inventor: Dean Kamen, Bedford, NH (US)

(73) Assignee: DEKA Products Limited Partnership, Manchester, NH (US)

( * ) Notice: Subject to any disclaimer, the term of this patent is extended or adjusted under 35 U.S.C. 154(b) by 433 days.

(21) Appl. No.: 12/014,382

(22) Filed: Jan. 15, 2008

(65) Prior Publication Data
US 2008/0198012 A1    Aug. 21, 2008

Related U.S. Application Data

(60) Provisional application No. 60/880,577, filed on Jan. 15, 2007.

(51) Int. Cl.
*G08B 13/14* (2006.01)
(52) U.S. Cl. .................................. 340/572.1; 600/365
(58) Field of Classification Search ............. 340/572.1, 340/10.1; 604/890.1; 600/300, 365; 128/921
See application file for complete search history.

(56) References Cited

U.S. PATENT DOCUMENTS

| | | |
|---|---|---|
| 5,233,520 A | 8/1993 | Kretsch |
| 5,412,560 A | 5/1995 | Dennison |
| 5,412,564 A | 5/1995 | Ecer |
| 5,478,989 A | 12/1995 | Shepley |
| 5,819,735 A | 10/1998 | Mansfield |
| 5,841,115 A | 11/1998 | Shepley |
| 5,979,757 A | 11/1999 | Tracy et al. |
| 6,024,281 A | 2/2000 | Shepley |
| 6,123,259 A | 9/2000 | Ogasawara |
| 6,199,753 B1 | 3/2001 | Tracy et al. |
| 6,283,914 B1 | 9/2001 | Mansfield |
| 6,317,722 B1 | 11/2001 | Jacobi |
| 6,386,450 B1 | 5/2002 | Ogasawara |
| 6,550,672 B1 | 4/2003 | Stoll |
| 6,587,835 B1 | 7/2003 | Treyz |
| 6,588,670 B2 | 7/2003 | Bukowski |

(Continued)

FOREIGN PATENT DOCUMENTS
EP        0601064        10/1997
(Continued)

OTHER PUBLICATIONS

International Search Report with Written Opinion dated Aug. 1, 2008, received in international application No. PCT/US08/51074, 8 pgs.

(Continued)

*Primary Examiner* — Toan N Pham
(74) *Attorney, Agent, or Firm* — Michelle Saquet Temple

(57) ABSTRACT

A medical device is disclosed. The medical device includes an RFID reader for receiving information from at least one RFID transponder. The medical device also includes a memory for storing a database and at least one processor for processing information. Also, a remote controller for a medical device is disclosed. The remote controller includes an information receiver for receiving information related to food. The infusion device also includes a memory for storing a database and at least one processor for processing information. A method for use in a medical device is also disclosed. The method includes receiving information from an RFID transponder related to food. Also, the processing the information by comparing the information to a database is included in the method. The method also includes determining the acceptability of the food and providing information related to acceptability to the user.

17 Claims, 16 Drawing Sheets

U.S. PATENT DOCUMENTS

| | | | |
|---|---|---|---|
| 6,652,455 B1 * | 11/2003 | Kocher | 600/300 |
| 6,847,899 B2 | 1/2005 | Allgeyer | |
| 6,852,104 B2 | 2/2005 | Blomquist | |
| 6,903,656 B1 | 6/2005 | Lee | |
| 7,063,263 B2 | 6/2006 | Swartz et al. | |
| 7,107,221 B1 | 9/2006 | Tracy et al. | |
| 7,617,132 B2 * | 11/2009 | Reade et al. | 705/27 |
| 2001/0014868 A1 | 8/2001 | Herz | |
| 2002/0027164 A1 | 3/2002 | Mault | |
| 2002/0050526 A1 | 5/2002 | Swartz | |
| 2002/0069131 A1 | 6/2002 | Miyata | |
| 2003/0032867 A1 | 2/2003 | Crothall et al. | |
| 2003/0132298 A1 | 7/2003 | Swartz | |
| 2003/0160683 A1 | 8/2003 | Blomquist | |
| 2003/0163223 A1 | 8/2003 | Blomquist | |
| 2004/0172301 A1 | 9/2004 | Mihai | |
| 2005/0022274 A1 | 1/2005 | Campbell | |
| 2005/0030164 A1 | 2/2005 | Blomquist | |
| 2005/0036395 A1 | 2/2005 | Maejima et al. | |
| 2005/0038680 A1 | 2/2005 | McMahon | |
| 2005/0038718 A1 | 2/2005 | Barnes et al. | |
| 2005/0040230 A1 | 2/2005 | Swartz et al. | |
| 2005/0065760 A1 | 3/2005 | Murtfeldt | |
| 2005/0071234 A1 | 3/2005 | Schon | |
| 2005/0143864 A1 | 6/2005 | Blomquist | |
| 2005/0165784 A1 | 7/2005 | Gomez | |
| 2005/0218218 A1 | 10/2005 | Koster | |
| 2005/0245904 A1 | 11/2005 | Estes et al. | |
| 2006/0010098 A1 | 1/2006 | Goodnow | |
| 2006/0074279 A1 | 4/2006 | Brover | |
| 2006/0081653 A1 | 4/2006 | Boland | |
| 2006/0125604 A1 | 6/2006 | Vaiana | |
| 2006/0129476 A1 | 6/2006 | Chin | |
| 2006/0167345 A1 | 7/2006 | Vespasiani | |
| 2006/0205564 A1 | 9/2006 | Peterson | |
| 2006/0219780 A1 | 10/2006 | Swartz et al. | |
| 2006/0276771 A1 | 12/2006 | Galley | |
| 2008/0030309 A1 * | 2/2008 | Darrouzet | 340/309.7 |
| 2009/0227855 A1 | 9/2009 | Hill et al. | |

FOREIGN PATENT DOCUMENTS

| | | |
|---|---|---|
| EP | 1622059 | 7/2005 |
| EP | 1677226 | 7/2006 |
| GB | 2414844 | 12/2005 |
| WO | WO9304449 | 3/1993 |
| WO | WO0043912 | 7/2000 |
| WO | WO0189368 | 11/2001 |
| WO | WO0221426 | 3/2002 |
| WO | WO03053498 | 7/2003 |
| WO | WO03061366 | 7/2003 |
| WO | WO03100740 | 12/2003 |
| WO | WO2004093648 | 11/2004 |
| WO | WO2005079161 | 9/2005 |
| WO | WO2005119524 | 12/2005 |
| WO | WO2005119590 | 12/2005 |

OTHER PUBLICATIONS

Supplementary European Search Report, dated Dec. 17, 2009, received in European Patent Application No. 08713772.5, 8 pgs.

* cited by examiner

DEVICE AND METHOD FOR FOOD MANAGEMENT

RELATED APPLICATIONS

This application claims the benefit of Provisional Patent Application No. 60/880,577 filed Jan. 15, 2007 which is incorporated herein by reference.

TECHNICAL FIELD

The present invention relates to food management and more particularly, to a device and method for food management.

BACKGROUND INFORMATION

Various people work to manage food everyday. Accordingly, there is a need for a device and method for food management.

SUMMARY

In accordance with one aspect of the present invention, a medical device is disclosed. The medical device includes an RFID reader for receiving information from at least one RFID transponder. The medical device also includes a memory for storing a database and at least one processor for processing information.

Some embodiments of this aspect of the invention include one or more of the following. In some embodiments, the medical device is an infusion device. In some embodiments, the medical device is a remote controller for a medical device. In some embodiments, the medical device is a glucose monitoring device. In some embodiments, the database includes user profile information. In some embodiments, the database includes information relating to food. In some embodiments, the database is a learning database. In some embodiments, the device also includes a display for displaying at least a portion of the information.

In accordance with one aspect of the present invention, a remote controller for a medical device is disclosed. The remote controller includes an information receiver for receiving information related to food. The infusion device also includes a memory for storing a database and at least one processor for processing information.

Some embodiments of this aspect of the invention include one or more of the following. Some embodiments include where the information receiver is an RFID reader. Some embodiments include where the information receiver is a bar code reader. Some embodiments include where the information is a unique alphanumeric code communicated to the device using a manual input device. Some embodiments include where the manual input device includes a capacitance slider. Some embodiments include where the manual input device includes at least one button.

In accordance with one aspect of the present invention, a method for use in a medical device is disclosed. The method includes receiving information from an RFID transponder related to food. Also, processing the information by comparing the information to a database. The method also includes determining the acceptability of the food and providing information related to acceptability to the user.

Some embodiments of this aspect of the invention include one or more of the following. In some embodiments, the method also includes where the processing further includes comparing the information to a food item and user profile database. Some embodiments also include where calculating a recommended amount of said food for user to ingest based on at least one blood glucose value. Some embodiments include inputting an estimate of the amount of the food item to be ingested by the body of the user and calculating an estimated bolus amount of insulin required by the body of the user based upon at least one blood glucose value. Some embodiments of the method include inputting at least one blood glucose value and calculating a recommended amount of the food item for user to ingest based at least upon the at least one blood glucose value. Some embodiments of the method include inputting an estimate of amount of the food item to be ingested by the body of the user and calculating total caloric intake by the user based on a sum of the inputs during a period of time.

These aspects of the invention are not meant to be exclusive and other features, aspects, and advantages of the present invention will be readily apparent to those of ordinary skill in the art when read in conjunction with the appended claims and accompanying drawings.

BRIEF DESCRIPTION OF THE DRAWINGS

These and other features and advantages of the present invention will be better understood by reading the following detailed description, taken together with the drawings wherein.

DETAILED DESCRIPTION OF THE PREFERRED EMBODIMENTS

Figure 1A:
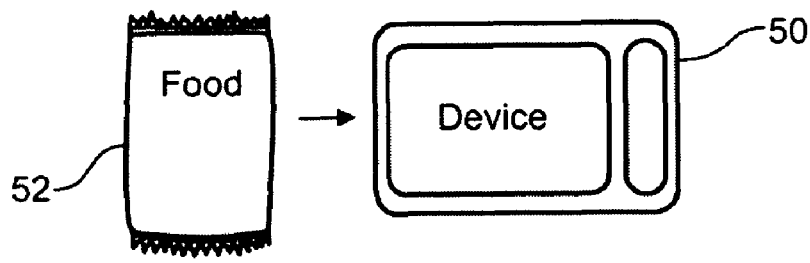
FIGS. 1A-1D are illustrations of various embodiments of the relationship between food items the device.

The device and methods described herein relate to interaction with food items, either directly or indirectly, in order to manage the food items. Food items include any prepared food, menu items or individual item or items that are edible. The device includes an electronic medical device having any one or more of the following: a memory, processor, screen, housing, wireless communication device, a speaker, a vibration motor, a power supply, a speaker, a radio, a camera, software running a user interface, a housing, an input mechanism, bar code scanner, camera, and/or RFID reader. Medical devices include but are not limited to: glucose meters, continuous glucose monitor handheld device, remote controllers for medical devices including infusion devices and/or continuous glucose monitors, and infusion devices including insulin pumps. In one embodiment, the medical device is a remote controller device for an infusion pump where the remote controller device includes a glucose meter.

Other electronics devices may be used including but not limited to, a consumer electronic device. Consumer electronic devices include but are not limited to any device with the capability to receive information. The medical devices or other electronic devices may receive information through any means including but not limited to an RFID reader, a bar code scanner, manual input using a capacitance slider, pad, touch screen, button or buttons. The consumer electronics devices include, but are not limited to, a personal data assistant (PDA) either with or without internet or email service, a watch, a cell phone.

The electronic devices or medical devices interact with the food items in various levels and with various management capabilities. The various interactions are described herein separately, however, it should be understood that one or more, in any combination, can be performed by the same electronic or medical device.

In one embodiment, the electronic device or medical device includes a database and/or is connected via wireless connection to a database that includes nutritional information about the food item. Additionally, the electronic device or medical device may include a database containing user profile information. This user profile database may be cross-referenced with the food database. Either or both databases may be learned databases. In another embodiment, the electronic device or medical device processes payment for the food item. In another embodiment, the electronic device or medical device alerts or alarms when a particular food item is available and/or within a particular distance from the electronic or medical device. In still another embodiment, the electronic or medical device, having access to biometric information either stored in the memory of the device or else accessible through wireless communication, suggests a food item or an interaction with a food item. In another embodiment, the electronic or medical device tracks the interaction with a food item.

There are a number of embodiments for the interaction between the food item and the electronic or medical device. Any of the following embodiments can be used in the devices, or methods, in any combination.

The interaction may be initialized by a signal sent from the food item to the electronic or medical device, e.g., a RFID transponder within the food item packaging or on a menu item is read by an RFID reader on the device. However, the interaction may be initialized by the electronic or medical device reading a bar code on the food item. The interaction may be initialized by a code being entered into the electronic or medical device manually, by a user. Additionally, the interaction may be initialized by an optical image being taken by the electronic or medical device of the food item. Also, the interaction can be initialized by a signal being sent from a device directly related to the sale of the food item, i.e., a vending machine or a store shelf (see smart shelves as described herein).

The electronic or medical device receives the information regarding the food item and may use this information in any one or more of a number of food management tasks. The tasks will be described separately, however, it should be understood that one or more of these tasks can be done to any one piece of food item information. In one embodiment, all of these tasks are performed. Additionally, the tasks described herein are meant to be limiting; other tasks will be readily understood to one of ordinary skill in the art. The tasks include informing of nutritional content, tracking food items, suggesting food items, suggesting user action in response to the ingestion of a food item, calculating caloric intake, calculating recommended amount, calculating bolus amount, signaling food items, purchasing food items, recommending food items, tracking inventory of food items, tracking location of food items, mapping Out location of food items, suggesting particular locations to find the food items, and many other tasks that will be described in more detail below.

Figure 1B:
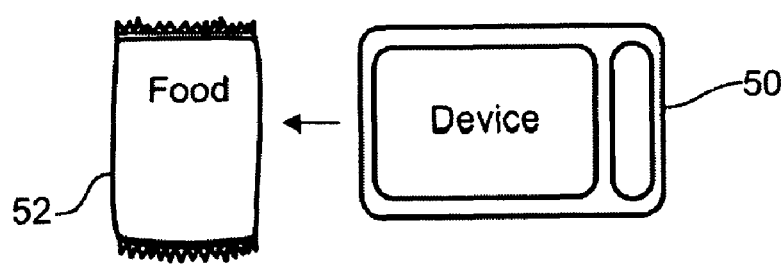

DEVICES. Referring first to FIGS. 1A-1D, the electronic device ("device") 50 used can be any device as described in more detail above. The device includes, at a minimum, an information input or receiver such that the device is able to identify the food item. In FIG. 1A, the food item "calls out" to the device, i.e., the food item 52 may contain an RFID transponder and the device 50 may contain an RFID reader. In FIG. 1B, the device 50 "calls out" to the food item 52. In this embodiment, the device 50 may include a bar code scanner, a magnetic strip reader or a camera capable of identifying the food item 52. Also, the embodiment shown in FIG. 1B represents where the device 50 receives a manual input of a code or other that identifies the food item 52.

Figure 1C:
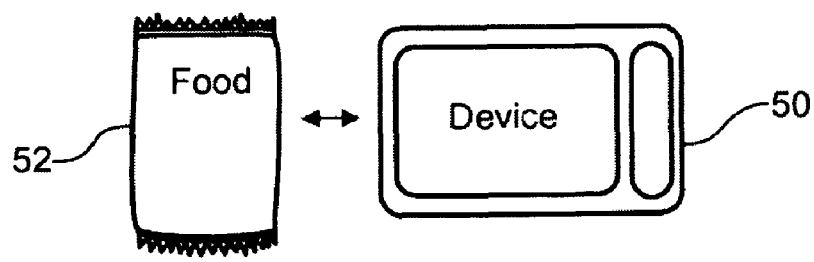

Referring to FIG. 1C, in this embodiment, the device 50 and food item 52 have bidirectional communication. In this embodiment, both the food item is capable of "calling out" to the device 50 and the device 50 is capable of "calling out" to or identifying the food item 52.

Figure 1D:
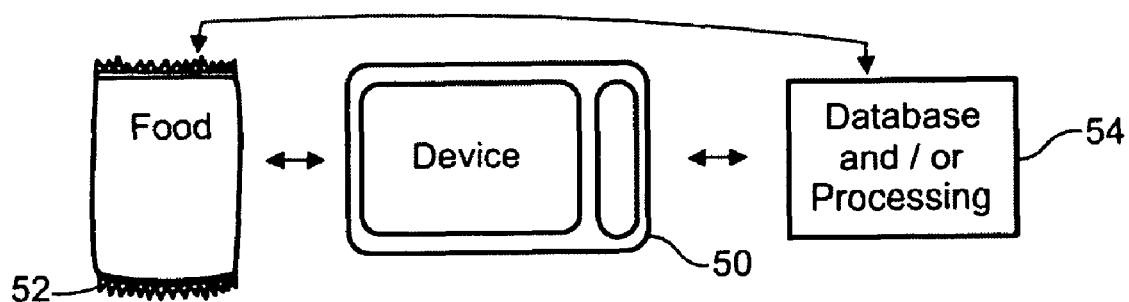

FIG. 1D represents an embodiment where the device 50 may communicate with the food item 52, and/or the food item 52 may communicate with the device 50, but the device 50 and/or the food item 52 may also communicate with a database and/or processing facility 54. Thus, the database 54 may be within the device 50 itself, or remotely accessible via wireless communication between the device 50 and the database and/or processing facility 54. The database 54 contains information about the food item 52 and/or about the user (a "user profile" database). The database and/or processing facility 54 may also communicate with a food item 52, updating the information the food item 52 communicates, e.g., updating the information contained on the RFID transponder. In some embodiments, the database is a learned database.

Figure 2A:
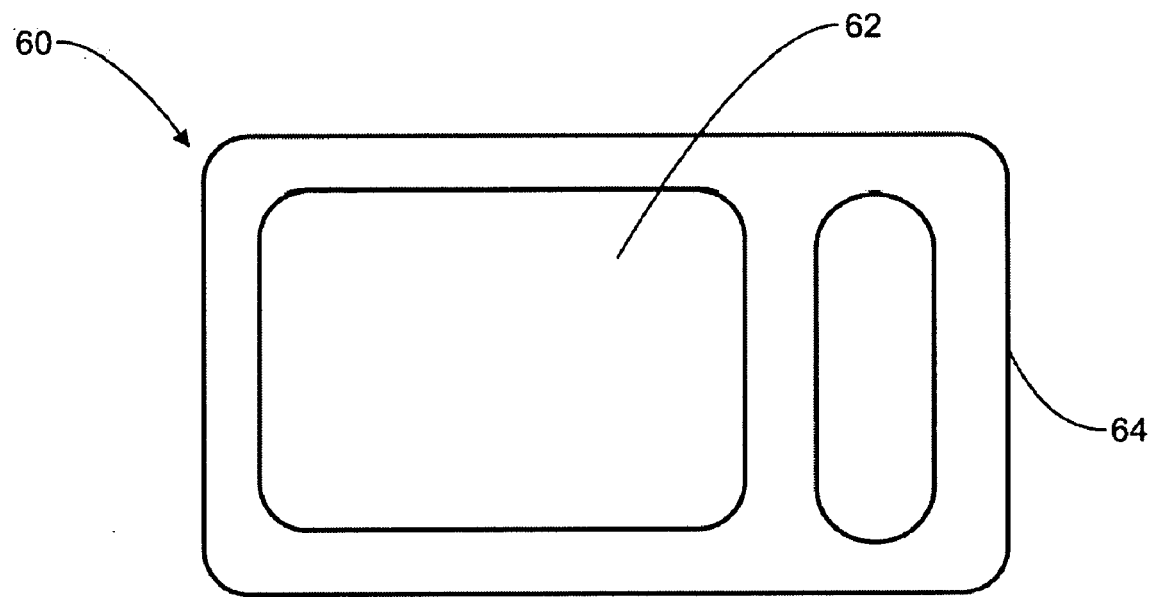
FIG. 2A shows one embodiment of the device.

Referring now to FIG. 2A, in some embodiments, the device is any electronic device 60, but in the exemplary embodiment, the device includes a display 62, a CPU (not shown), a power supply (not shown), a housing 64 as well as at least one technological means (not shown) for communication with the food item. For example, this technological means includes, but is not limited to, a camera, a radio and/or a bar code reader, and/or wireless communication with a database, and/or manual input of an identification code.

In some embodiments, the device also includes a speaker or a vibration motor to signal to the user. Also, in some embodiments, the device includes one or more manual input devices, for example, a capacitance slider, buttons, keypad, scroll wheel, jog wheel, or any other input device. In still other embodiments, the device includes a GPS device. In some embodiments, the device includes at least one database. In other embodiments, the device includes optical character recognition software.

Figure 2B:
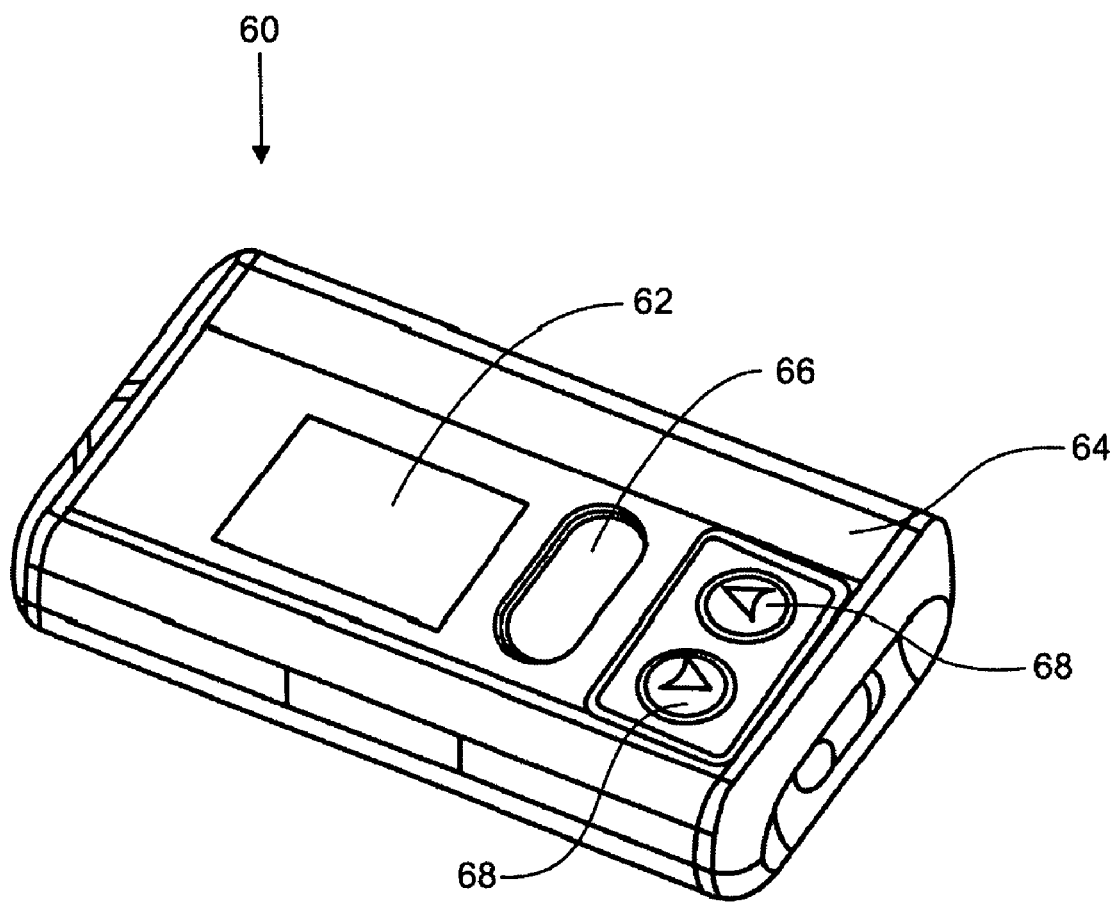
FIG. 2B is a top view of one embodiment of the medical device.

Referring now to FIG. 2B, in this embodiment, the device 60 is a medical device. In one embodiment, the medical device is an infusion device. In the embodiment shown in FIG. 2B, the infusion device 60 includes a display 62, a housing 64 and manual input elements, a capacitance slider 66 and buttons 68. In other embodiments, the device 60 may include only one of these manual input elements, but in other embodiments, the device 60 includes all shown. As described above, the device 60 additionally includes at least one technological means for communication with the food item. In some embodiments, this technological means is an RFID reader, however, in other embodiments; the technological means is any of those described above.

Figure 2C:
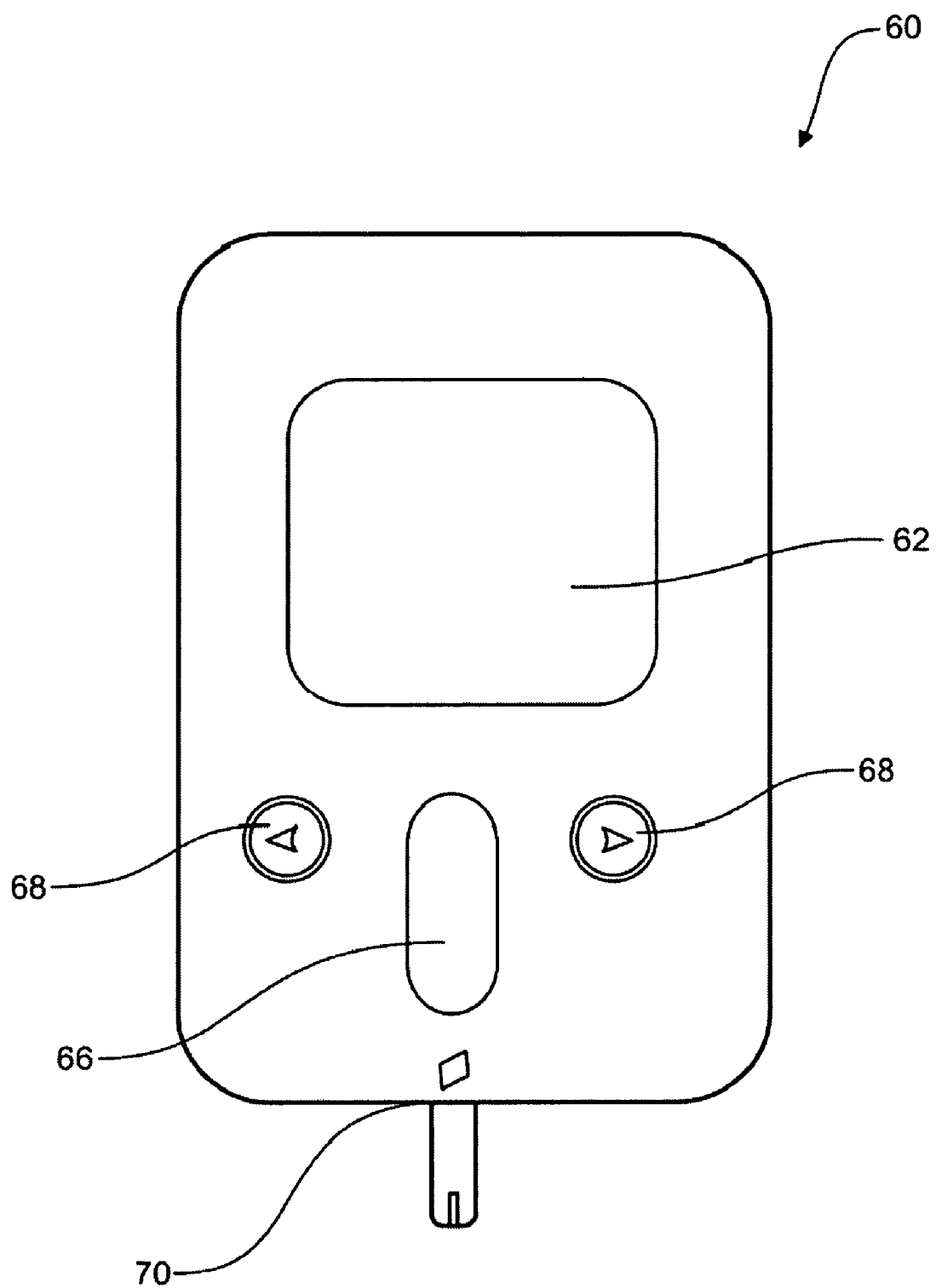
FIG. 2C is a front view of one embodiment of the medical device.

Referring now to FIG. 2C, in this embodiment, the device 60 is a medical device. In one embodiment, the medical device is a remote controller for a continuous glucose monitor and/or for an infusion device. The controller device 60 includes a display 62 and a housing 64. The controller 60 may also include at least one manual input device 68. In other embodiment, a slider (as shown in FIG. 2B) may be included. As described above, the device 60 additionally includes at least one technological means for communication with the food item. In some embodiments, this technological means is an RFID reader, however, in other embodiments; the technological means is any of those described above.

Also, in one exemplary embodiment, the controller 60 includes a strip glucose reader (i.e., a glucose meter) 70. In one exemplary embodiment, the controller 60 is a remote controller for an infusion device, e.g., an insulin pump. In one embodiment, the controller 60 is a continuous glucose monitor handheld/controller. In still another embodiment, the controller 60 is a both a remote controller for a infusion device and a controller for a continuous glucose monitor.

The controller 60 embodiment includes the capability of transferring information or commands to the medical device (e.g., insulin pump) based on the food information. For example, the controller 60 may access information related to the food item from a database internal to the controller, and the user inputs a desired amount of ingestion. The controller 60 may, using the food item information, calculate the amount of bolus the user should infuse to cover the requested amount of food item. This bolus amount can then be remotely sent to the insulin pump worn by the user and the insulin pump will then infuse that bolus amount of insulin into the user.

Other methods include the user entering a blood glucose reading (i.e., in the embodiment shown in FIG. 2C, the user uses the strip reader to determine the blood glucose, thus, the reading is already in the controller 60, or, in the case where the controller 60 is a controller for a continuous glucose monitor, again, the controller 60 already has the user glucose reading) and the controller 60 recommends a food item and/or an amount of a food item identified to the controller 60 based on the food item and blood glucose reading.

Various embodiments are shown in the figures. However, these are not limiting, as other embodiments containing combinations of the elements described above will be apparent to one of ordinary skill in the art.

Figure 3:
FIG. 3 is illustrative view of the communication between an RFID reader on a device and a food item.

In some embodiments, the electronic or medical device is designed to read an identifying device on the food item or associated with the food item, giving identification. Referring to FIG. 3, in one embodiment, the device 50 receives information from the food item 60 and reads the identification of the food item. In this embodiment, the device 50 includes an RFID reader and the food item 60 includes an RFID transponder. The food item information communicated to the device is described in more detail below, however, can be any information; including but not limited to nutritional information, price information, and/or location. In some embodiments, where the device 50 is within a communicable range from a food item 60, the food item will "call out" to the device and the device will "wake up" or otherwise signal to the user that a food item 60 is nearby. Where a food item 60 includes an RFID transponder, the radio signal is broadcast continuously. However, a device 50 may be programmed to wake-up or signal to the user where the food item 60 within communicable distance is one selected by the user in the "user profile database". Thus, the device 50 may be customizable to only signal to the user where the user is within a pre-selected distance to pre-selected food items.

Figure 4A:
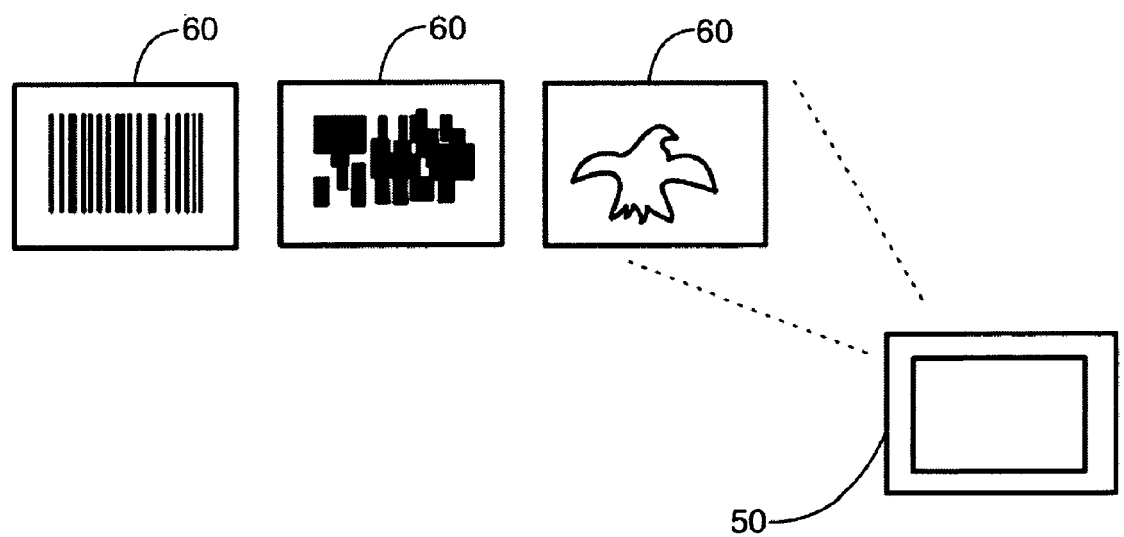
FIG. 4A is an illustrative view of various embodiments of communication between a food item and a device.

Referring now to FIG. 4A, other technological means of the device recognizing a food item are shown. The means shown in FIGS. 3-4A are not meant to be an exhaustive list of means, but are a few embodiments. Included in FIG. 4A are bar codes where the device 50 includes a bar code scanner and can read the bar codes from the food items 60. Optical recognition codes where the device 50 includes a reader, and where the device 50 includes a camera and the device recognizes the item through optical recognition. Any means of identification or transferring the food item information is available in alternate embodiments.

As described above, the device may be any consumer electronic device or a medical device. Consumer electronic devices include a cell phone, PDA, watch, an iphone, an icart, or a dedicated terminal.

The type of technological means for communication in the device varies depending upon the desired means for communications. For example, if the desired communication is through wireless communication, then a radio may be used. If the desired communication is through bar code, then a bar code scanner may be used. If the desired communication is through optical recognition, then a camera may be used.

The device housing can be any shape or size desired. The housing can be made from plastic, aluminum or any other type of material. Additionally, the housing can be shaped to fit within any holding device. The CPU can be any size desirable size and call include any type of software. The device can also include RAM of any size. As discussed above, in some embodiments, the device includes a feature for manual entry of information. This feature can be a capacitance slider or pad, at least one button or a keypad, a scroll or jog wheel, etc. In other embodiments, any feature allowing manual user interaction with the device is considered.

FOOD ITEMS. The devices described above are used in a food management capacity. However, in some embodiments, the devices include additional functionality other than food management. Also, it will be understood that although the functions, methods and systems described herein are described with respect to food management, in other embodiments, the devices described herein can be used to manage anything, including any type of consumer product. However, as an exemplary embodiment, use of the device, system and methods will be described herein with respect to food management. Other embodiments will be readily apparent to one of ordinary skill in the art.

The food item to be managed will either communicate directly with the device or indirectly with the device. In either embodiment, information regarding the food item will be imparted to the device.

As used herein, the term food item includes any edible item, whether in whole or part, and whether in a natural or artificial state. In some instances, the food item is entirely or partly artificial, i.e., not naturally occurring. The food item need not be nutritive, but can be non-nutritive. However, in all the cases, the food item is capable of ingestion by an animal.

Thus the food items includes vitamins, supplements, flavorings, colorings, herbal, prepared, frozen, fresh, raw, dried or powdered food items as well as beverages, which include juice, waters, milks, spirits, teas, coffees, carbonated sodas and any other drinkable substance. Other types of food items are contemplated including any item, whether regularly referred to as food or otherwise, capable of ingestion by an animal including a human.

Information regarding the food item includes nutritional information, serving size information, inventory information, location, pricing or other information, for example, pairing and volumes of food items that are put together in a beneficial manner, for instance, in a recipe or pairing a cheese or dish with a wine. Additionally, information related to recommendation for ingesting is also included in some embodiments.

The food item can be a food item in a vending machine, on a store shelf or in a particular pre-prepared dish, for example, in a restaurant. However, the food item can be any food item in which a consumer is contemplating buying or ingesting either presently or at a later. In other embodiments, the food item is not contemplated by the consumer but rather, the device recommends the consumer buy or ingests the food based on pre-programmed parameters, which will be discussed in greater detail below.

It should be understood that the term consumer includes an individual person, or a company or organization. The food item is not necessarily being bought or ingested at the time the device presents information to the consumer or manages the food. It should be understood that the term food item means either the physical item itself or the item in name only.

SIGNALS. The food item interacts with the device through a signal. The signal can be a radio signal, a bar code, an electrical signal, an optical signal or any form of a manual input that identifies the food item to the device. Thus these signals can be, but are not limited to, radio, electronic, optical, manual or bar code.

The signal can be automatic or requiring instigation by either the food item or the device. Thus, the signal between the food item and the device may be instigated by the food item when the device comes within a predetermined distance of the food item. In another embodiment, the device may request the information regarding a food item.

The signal may include any amount of information. Information includes, but is not limited to, an indication that the food item is within proximity, nutritional information, ingredients information, pricing information, recommendation information, acceptability, or that the food item exists.

The signal may include the entirety of the information of the food item to the device, or in other embodiments, the signal relates to an entry in a database. In this embodiment, the signal will trigger information from a database to be sent to the device. In some embodiments, the information sent is all of the information the database has on the food item. In other embodiments, the information sent is only a part of the information. The part sent is dependent on parameters entered into the device or the database and is based on the user desires (e.g., part of the "user profile"). For example, in some embodiments, the user may only desire information that the food item exists. In other embodiments, the user desires knowledge of the number of the food items existing in a particular location. In other embodiments, the user desires pricing information only. In other embodiments, the user desires carbohydrate information of the food item. In other embodiments, the user desires knowledge of the presence of a particular ingredient in the food item. In other embodiments, the user desires information of whether the food item is included in their pre-programmed diet management program and/or whether the food item conflicts with a diet management program or interacts with a drug the user is taking. All of these embodiments can found in certain embodiments in any combination, and still, other embodiments regarding the particular information on the device are contemplated. These embodiments are discussed in further detail below. Still other embodiments are contemplated that will be apparent to one of ordinary skill in the art.

In some embodiments, the signal may be manually entered into the device. In this case, the manual entry triggering identification of the food item can vary from a UPC code to any alphanumeric, purely alpha or purely numeric code in any length varying from 1 to any number of significant figures. The entry may include a system designed specifically for a particular brand of food, or for a particular type of dietary management. The combination to be entered into the device may be located on the food item itself, or may be available as a look-up table on the device. In other embodiments, the entry may be anything that is pre-assigned and determinable by a user.

In one embodiment, the user manually enters a 3 digit alpha numeric code located on the food item, followed by the number of serving sizes. The number of serving sizes can either be the number in the food item they are purchasing, or the number in the food item they are planning on eating. In any case, the 3 digit alphanumeric code will present the user with food item the pre-determined food item information, including, in some embodiments, recommended serving size. In alternate embodiments, the code is a 2-digit code, or a 2 digit alphanumeric code. In some embodiments, the code is a product or brand specific code. In still other embodiments, the code is located on the product itself, or is a look up in a database.

INFORMATION. As described above, the information regarding the food items varies with the embodiments. The information can be any information a user desires with respect to the food item. The information communicated in response to the signal is pre-determined, i.e., based on user parameters or other parameters, for example, a particular company, store or organizations parameters.

As described above, the information may vary anywhere from an indication of the presence of the food item, to detailed information regarding the food item or anything related to the food item. In the embodiments where only the presence of the food item is indicated in the signal, the device may alarm (audio or vibration), wake-up, light up, or otherwise indicate through the UI or visual, audio or other signal the presence of the food item. In other embodiments, the presence of the food item is either solely or additionally, indicated through a light, alarm or other, indication on a store shelf, vending machine or other location where a food item can be displayed or through any means where a food item can be sold (i.e., on a menu or other).

However, in those embodiments, either in addition to the signal that the food item is present or on its own, additional information is communicated. It is these embodiments that will be described in more detail below. Again, these embodiments may be in additional to the signal of the presence of the food item or in lieu of same.

The information itself is either stored in a database or communicated directly through the signal. Thus, in the embodiment where the signal is sent via RFID, or radio communication, the signal may include a code or identification of the food item which is then used to pull-up, look-up or otherwise, information in a database related to that food item, or, in alternate embodiments, the food item information is directly communicated in the RFID or radio signal.

THE DATABASE. The database may be located anywhere in which the device can access the information contained on the database. In one embodiment, the database may be located on the device. In other embodiments the database may be located on a network, either the internet or an area network. In the embodiments where the database may be located remotely, the database may be accessed via a wireless signal. In some embodiments, although the database may be stored on the device itself, the database may be updated via wireless or wired connected to the database elsewhere, thus, additional information may be accessed when requested or updated automatically.

Thus, the device may retrieve the food item information either by accessing it through a wireless connection or by retrieving the information from its internal RAM. The RAM is either part of the CPU, or addition RAM is added separately.

The database may contain information related to the food item for use in food item management. The information includes, but is not limited to, that related to nutritional or ingredient information, price, location of items, etc, described in more detail above. However, the information may also include information that is user specific or demographic specific. For example, the database may contain information related to the preference of the particular food item for those with specific diet restrictions. These include, but are not limited to, those living with diabetes, those with high-blood pressure, high cholesterol, overweight, specific allergies. Depending on the user, different information will be sent to the device for the user to view.

The database may be used to track a user's habits, preferences, intake or any combination thereof. The database may be used to suggest food items in response to a specific inquiry, i.e., based on a user entered preference or request. In one embodiment, the database is a learning database.

The database includes information on from 1 food item to every food item possible on the earth. The database can include any and all possible information related to any one or more particular food item.

Each user of the database is identified in the database and has particular preferences recognized by the database. This is referred to as the user profile. The database presents information related to the food item based on the user profile. The term "user" means an individual user; a group of users, a company, an organization, a subset or any other combination or type of predetermined subset.

These user profiles may be predetermined or learned. Thus, in the embodiment where the user is an individual, the user profile is particular to that user. In the case where the user is an identifiable group, the user profile is predetermined by one representing the entire group.

Thus the device, together with the database, is used in food management. The device is capable of identifying the food item, and capable of determining specific information regarding that food item either internally (if the device received the information via signal transmission from the food product itself or in the case where the device includes a database containing information for the food items) or indirectly through wireless communication with a database.

USER PROFILE. In addition to the description above, the user profile may be entered through the central system, for example, a web page. The user may update their profile or view it at any time using the internet. In some embodiments, any person may access or create their user profile. In other embodiments, the user must be part of a private group to access or create a profile. The profiles may be accessed by any database programmed to do so. If the profiles are available on a web server, the profiles may be accessed anywhere. However, in some embodiments, the device itself independently contains or stores the user profile and the database. Thus, in these embodiments, the device may access only one profile.

The user profile may include but are not limited to information relating to medical conditions, including allergies and diseases. Also, the user profile may include, but is not limited to, any one or more of the following: preferences, goals, and choices for the device to alarm, limit, prevent or recommend, are amongst other user profile options.

The user profile, in some embodiments, additionally may include financial information. This can include a budget or an allowance, as well as an account. The device may be used as an electronic bank where the user may transfer funds to a vending machine or a store to purchase food items. Additionally, because the user profile includes a number of user chosen limitations, those limitations may optionally be linked to the account, preventing actual purchasing of particular food items. In one embodiment, the financial information in the user's profile is controlled by a separate party, for example, a parent or guardian of the user may control the finance of the user profile. In still other embodiments, a third person has full control over a user's profile. This can be a parent, guardian or a doctor or other medical professional.

FOOD MANAGEMENT. The combination of the food items, information regarding the food item and the device allows for food management. The device and information may provide the ability of the user to purchase the food item, track the purchase of the food item, track the ingestion of the food item and determine information regarding the food item. The information also may provide suggestions of food items to the user of the device. The combination of having user preferences and information related to the food item allows for infinite combinations and possibilities for food management, all which will be apparent to those of ordinary skill in the art. Exemplary embodiments of the use of the system are described below.

MULTIPLE DEVICE FUNCTIONS. In some embodiments, as mentioned above, the device includes other functions. For example, the device may be a cell phone, a medical device, a PDA, an iPOD, MP3 player or any other electronic device. In the case when the device includes additional functions in addition to food management, the device may either integrate the food management function with the additional functions, or else include the food management function as an optional function.

MEDICAL DEVICE CONTROLLER EXAMPLE. In one embodiment, the device is a medical device controller, as shown in FIG. 2C. Although the example described below relates to the device being a medical device controller, in alternate embodiments, these same functionalities may be embodied onto an infusion device or insulin pump. In these embodiments, the blood glucose reading is either manually entered by the user, automatically updated based on a continuous glucose monitor or blood glucose reading taken by a glucose meter and automatically transferred to the insulin pump.

Figure 4B:
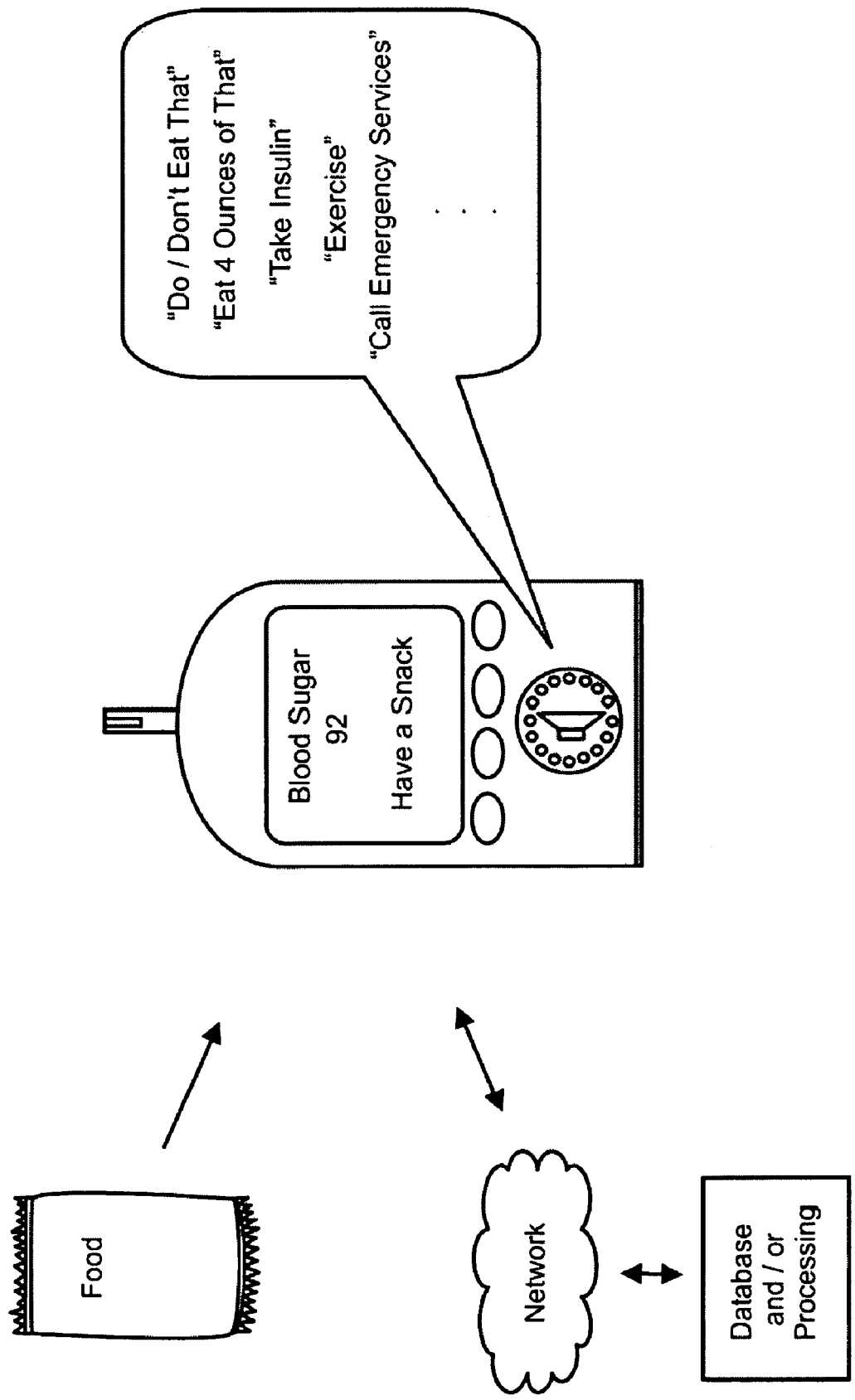
FIG. 4B is an illustrative view of one embodiment of a medical device interaction with a food item and information provided to the user.

Referring now to FIG. 4B, the food management system, in one embodiment, is integrated with the controller's other medical functionality. Thus, where the controller is a remote controller for an infusion device, e.g., insulin pump, the insulin controller includes, as part of its function, a tracking system of the amount of insulin on board, ("IOB") which is the amount of insulin in the user's body at any given time.

Using this information, as well as the information relating to the most recent blood glucose reading of the user and the user's specific insulin sensitivity information, the controller may calculate a recommended insulin dose for the particular user once the user enters the intended intake of nutrition. However, in other embodiments of the controller, the controller tracks blood glucose and/or provides a glucose meter, and additionally aids a person in selecting appropriate food items and serving sizes based, on blood glucose and caloric intake (but not insulin information).

The present system is integrated into the nutrition intake information. Thus, the device receives a signal relating to the food item that is going to be ingested by the user. The signal is generated through any means described above in the various embodiments. The controller then recognizes the food item and may access information relating to nutrition of that food item. Using that information, a calculator may determine the amount of insulin (bolus) needed.

In one embodiment, once the food item is received/recognized by the controller, additional information relating to the amount of the food item planned to be ingested will be requested from the user. In other embodiments, this information will only be requested where the food item includes greater than 1 serving size. In still other embodiments, the information will only be requested if the food item is generally not intended to be consumed by one person at one given meal or snack time.

In some embodiments, once the food item is received/recognized by the controller, along with the user's blood glucose reading, the user may request the controller to "suggest a serving size". This function will assist the user in determining the amount of any food item the user may ingest. In some embodiments, this determination is based solely on the blood glucose reading. In other embodiments, this determination is based on the blood glucose reading together with trend data for blood glucose readings. Additional factors the controller may take into consideration are accumulated caloric intake, exercise information and/or illness information. In some embodiments, the controller may additional request a body temperature reading or other additional information before calculating and recommending food items or quantities of food items.

In the various embodiments, these options may either be user options that are pre-set by the user, or can be pre-set and require the user to turn them off. In still other embodiments, the user preferences may include food items where the user requests the controller not to ask the serving size, and those food items where the user wishes the controller to prompt the user to enter the serving size (i.e., where the serving size is required).

The term "serving size" may mean the actual serving size determined by a food item producer, by a nutritional standard, or a recipe, or can refer to an entry of the weight, size or number of items a user intends to ingest. The database uses this serving size information to calculate the insulin dose recommended and/or, to track the user's food intake.

In some embodiments, the food management is performed by an insulin pump and controller system, where there is also continuous glucose monitor data collected by the controller (and/or pump) at intervals.

In some embodiments, the food management system utilizes a glucose meter as the device, and the user either enters the insulin they intake, or, in the case where the diabetic using the glucose meter is not also using insulin, information relating to other drug intake is entered. In some embodiments, functionality that is described above with respect to the insulin pump and/or controller is also imparted to a stand-alone glucose meter.

Additional functionality in the various embodiments of the insulin pump, insulin pump and controller, insulin pump and controller and glucose monitor, insulin pump and controller and glucose meter, or stand-alone glucose meter, include recommendation and limitation functionality. For example, the device, upon recognition of the food item, may determine the food item is either "acceptable" or "not-acceptable" for the user at that time (or anytime, depending on the user profile). This acceptability factor may be determined based on blood glucose readings, accumulated caloric intake, or both.

In addition to tracking food ingested by the user, in this embodiment, the food management system may additionally provide recommendations of food to be ingested or limit food intake. These recommendations are based on user preferences which are entered into the user profile. In this way, the profile may include recommended snacks, quantities or food items in response to particular blood glucose readings. Additionally, recommendations based on time of day or planned exercise may be made. Also, limitations based on the same profile may include limiting caloric intake to a maximum per day or per time period, limitations of certain foods, and making recommendations not to ingest food when the user has a particular range of blood glucose readings.

For example, the device may either receive a manual input of a glucose reading or receive it automatically. With respect to receiving the data automatically, this occurs where the device is implemented in an insulin pump remote controller with a glucose meter built in, or in the case of a controller that doubles as a continuous glucose monitor controller receiving regular readings from an injected glucose sensor (or, alternatively, on an insulin pump itself receiving either transmitted glucose readings either from an continuous glucose monitor or from a glucose meter, or otherwise manually entered). Readings may be in mg/dl or mmol/L. Where the reading indicates a low glucose reading, a message may appear to the user saying, for example, "eat a snack", or "do you want a snack?". The exact wording of the message may vary. Following a response from the user, the display may include a recommended snack, for example. "3 oz of orange juice". These messages may be pre-programmed by the user with their preferences. These comments may also be audio, audio and visual, and/or accompanied by a light or vibration or other alarm indication.

These comments may be accessed by someone other than the user as well. For example, if a diabetic looks unwell, a friend, family member or otherwise third party may view the device and see the message "do you want a snack?", select "yes" and the device will list to the third party a suggested snack or a number of options for a snack. Additionally, the device could include instructions to the third party of what to look for and how to help the diabetic.

Other embodiments include, upon the request of the user, a recommendation for a meal or a snack if the user is hungry. The user may select from a menu "I want a snack", or "I want lunch", or simply "I am hungry". In response, the device, knowing the user's medication intake and blood glucose level, as well as the time of day, can recommend a type of snack or a type of meal. Additionally, the device may recommend a list of options. For example, if the user's blood glucose level is within an acceptable range, when the user requests "I want a snack", the device may list a number of food options that will not affect the blood glucose level negatively. For example, a sugar free gelatin product, sugar free ice-pop, club soda, or other non-nutritive food items that may satisfy the user's craving without negatively impacting their blood glucose levels.

Additionally, where the device includes an RFID reader, the device may direct the user to a snack option in which the RFID reader has located based on an RFID transponder signal.

Also, if the user desires a snack, and the blood glucose readings indicate a range where it would be preferable for the user to eat a snack, the device may indicate a list of suggested snacks that the user had entered into the profile to be eaten when their blood glucose readings were within a particular range. Other options may be that the user may select "salty snack", or "crunchy snack", and the device may suggest preferable foods depending on the profile and blood glucose reading.

NEW DATABASES AND PROFILES. In one embodiment, the device may download category specific databases and profiles. For example, a user may download a specific database or register their device to receive access to a specific database. These specific databases may be diet specific databases, brand specific databases, goal specific databases or interest specific databases.

In some embodiments the databases are learning databases. Thus, the database learns a particular user's preferences and makes recommendations based on those preferences, or assists the user with making lists or planning based on past user preferences.

SMART VENDING MACHINES. One embodiment of the system is implemented with a vending machine capable of communicating with the device. The vending machine communicates the food items present. This communication is done using a transponder, or any signaling means discussed above. In some embodiment, the vending machine transmits the nutritional information, however, in other embodiments; the device references the database for nutritional information.

In some embodiments, the food items each include a transponder or RFID, and signal to the device. Thus, the RFID transponder is in the food item packaging in this embodiment.

In some embodiments, the device may be used to browse through the available products in the vending machine, and the user may view the nutritional information and price. The user may also receive recommendations from the device based on their user profile. These recommendations include those based on the food items ingested for the day, time of day and blood glucose readings, caloric or monetary allowance remaining, activity levels, etc. In some embodiments, the user may purchase the item in the vending machine using the device and the electronic account. In other embodiments) the user purchases a food item based on recommendations from the device, but manually purchases the item.

In some embodiments where third parties have put locks on the device, this device will only be able to purchase particular food items from the vending machine. Additionally, the device may track the calories and other nutritional information of the food items ingested through electronic purchase of the food items.

In some embodiments, as the vending machine is loaded, each slot is reprogrammed with the bar codes of the product, or through RFID transponders on the slots only (i.e., in this embodiments, the product packages themselves do not necessarily contain an RFID transponder, however, the slot where the products are loaded do contain an RFID transponder). The device recognizes the vending machine and knows the products located in each slot based on a database update. In this way, each vending machine may be loaded differently, thus, standardization is not required.

In addition, the device may communicate with an online database which may include up-to-date information regarding, for example, the location and contents of vending machines. Thus, as user may use the device to search for a particular food item, or for any recommended food items within a certain desired proximity of the location of the device.

In some embodiments, when the device is within a particular proximity to a vending machine, the vending machine may signal to the device and the device may alarm or otherwise indicate same to the user, either audio and/or vibration and/or visual and, in some embodiments, this indication may additionally contain a displayed ad or other message on the UI to signal to the user.

INCENTIVE PROGRAMS AND USER REWARDS. In some embodiments, incentive programs and user reward programs may be linked to the database and the buying patterns of the user. Thus, in these embodiments, the user profile may contain the user's preferences as well as buying and eating habits. The incentive program may electronically send messages or ads to the device to entice the user to desire the food item. These messages may be sent, for example, when the device is within a predetermined proximity to the food item, when the user indicates hunger or when the user is in a particular store, or at any time desired. Additionally, in some embodiments, particular brands or stores may have reward programs that track the number of brand or items purchased from a store or vending machine, and reward the consumer with coupons or electronic funds in their profile account for purchasing a particular number of food items.

Figure 5:
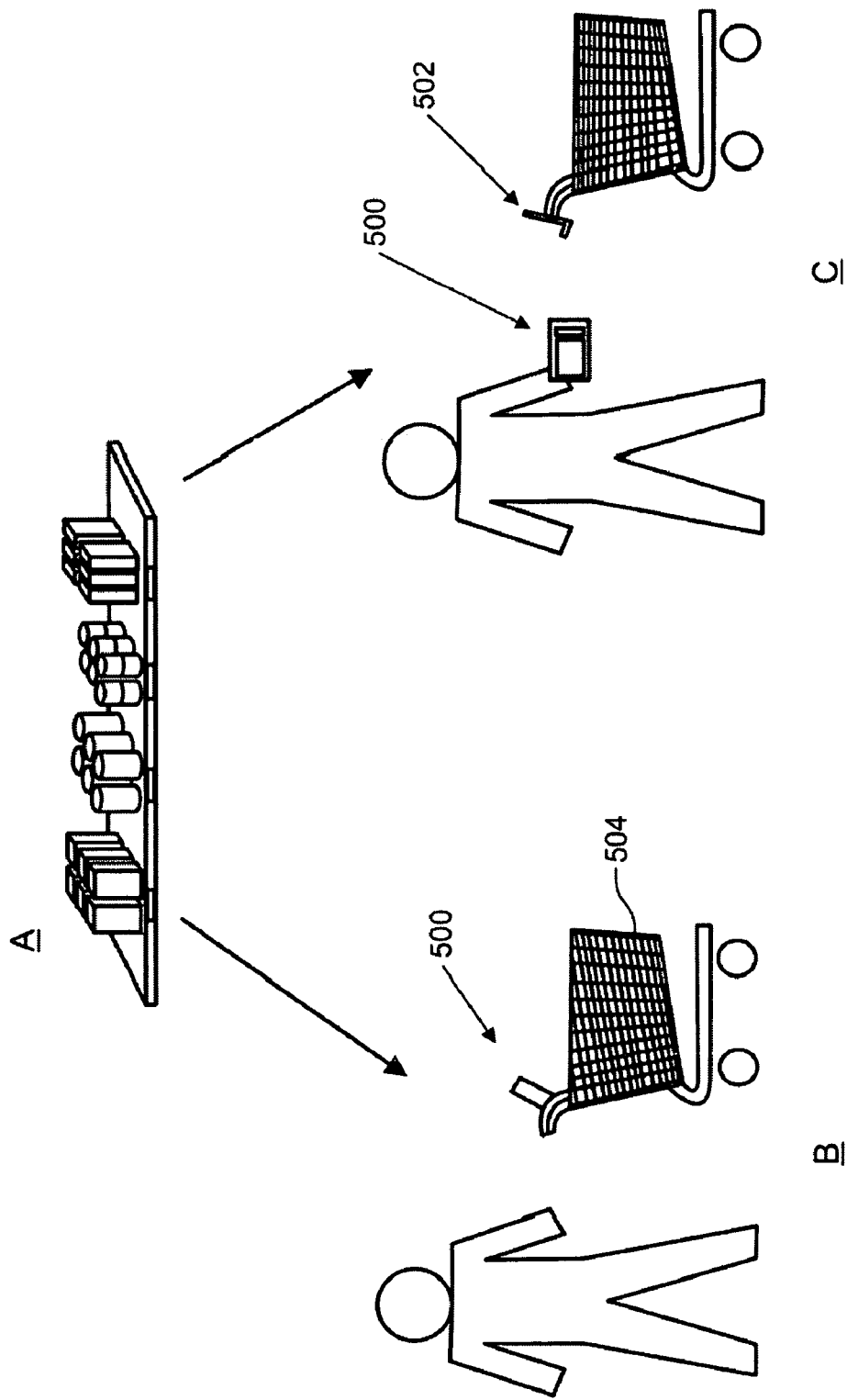
FIG. 5 is an illustrative view of various embodiments of the device in use while shopping.

SMART CART. One embodiment of the system is shown in FIG. 5. The device 500 is located on a shopping cart 504 or a shopping basket. In one embodiment, shown as "C" the shopping cart 504 or shopping basket includes a holster 502 allowing the consumer to arrive to a store and easily attach their device 500 to the shopping cart 504 or basket. In another embodiment, shown as "B" the user's device already has a holster that can attach to a shopping cart or basket and the user attaches the holster and device to the shopping cart or basket.

Figure 6:
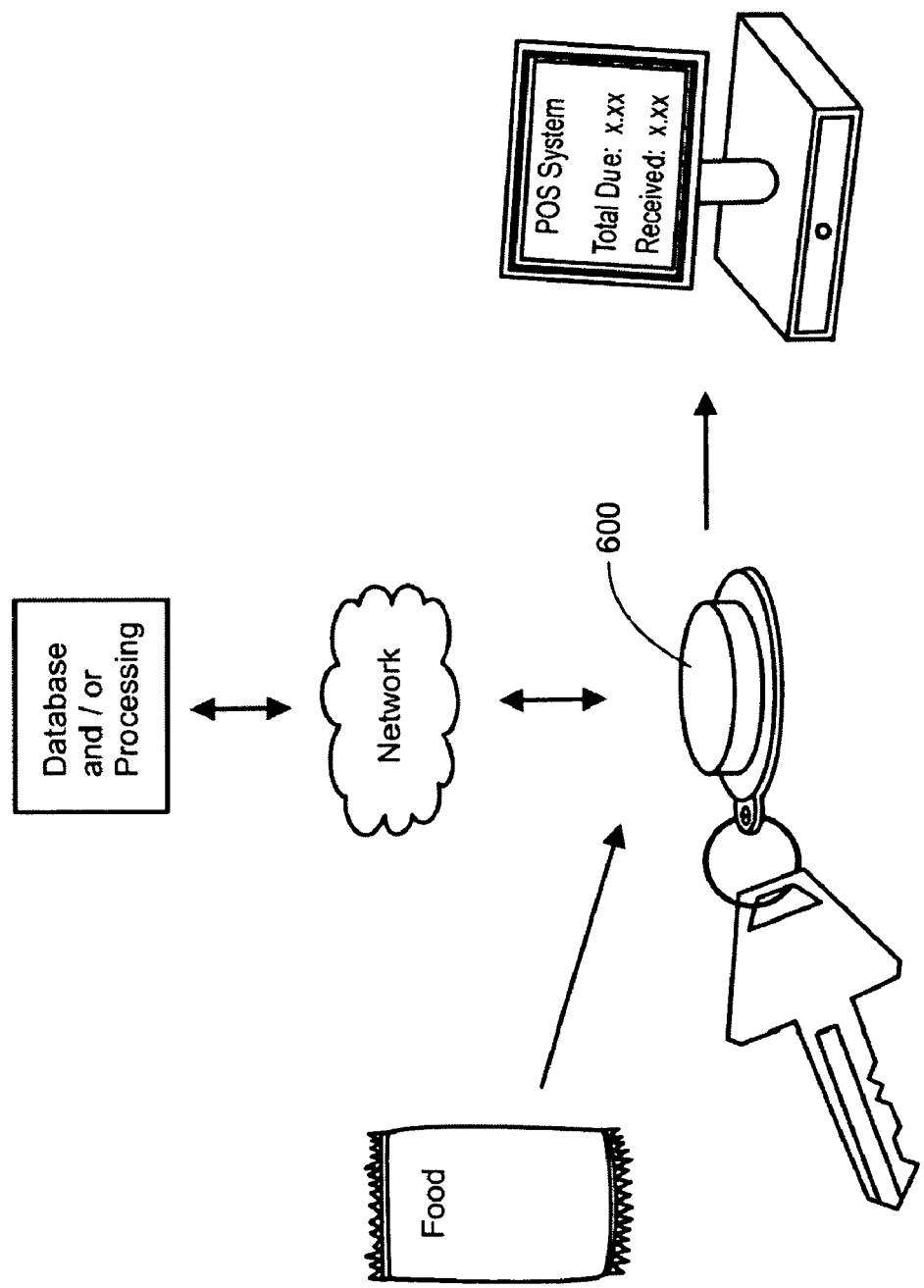
FIG. 6 is an illustrative view of another embodiment of the device in use while shopping.

In another embodiment, shown in FIG. 6 the device (not shown) is already attached to the shopping cart or basket (not shown). Using another embodiment of the device 600, here is shown as a key fob, however, in other embodiments, can be any device, the user identifies themselves to the device on the shopping cart or basket and the device recognizes the user and their profile. As shown in FIG. 6, this embodiment may be used such that the device on the cart may include a display and the consumer uses the device as they shop, however, upon check-out, the user's device 600 connects to the network and payment is made using the device 600

Referring again to FIG. 5, as the user passes food items within the store, the device may signal to the user either visually, audibly and/or by vibrating the device or the handle to the basket or shopping cart, that an item is within close proximity that may interest the user.

The items that will instigate this alarm will be those items in which the device recognizes as either user profile preferences, part of a user made list (described below) or items that the database recommends based on the user profile.

In one embodiment, the user may, upon entering the store and instigating the device, elect certain alarms or indications linked to store specials or preference items, or linked to a particular brand or genre (for example, organic, ethnic, or a company brand). In other embodiments, these are not options available to the user, but rather, pre-programmed in the device that is installed on the shopping cart or basket.

Figure 7A:
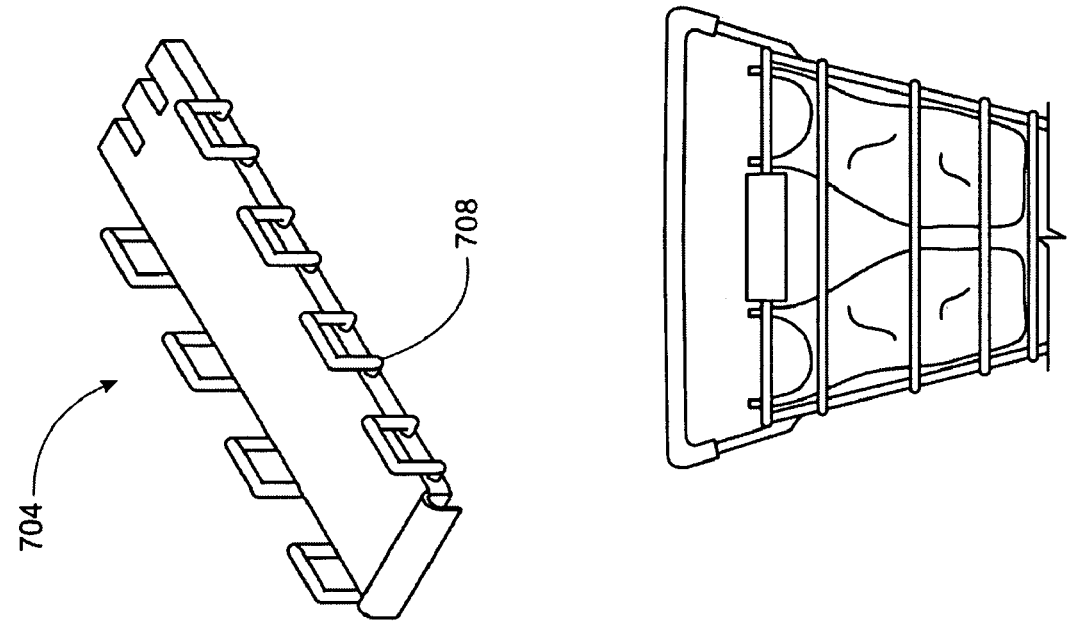
FIGS. 7A-7C show various embodiments of the bagging apparatus.
Figure 7A:
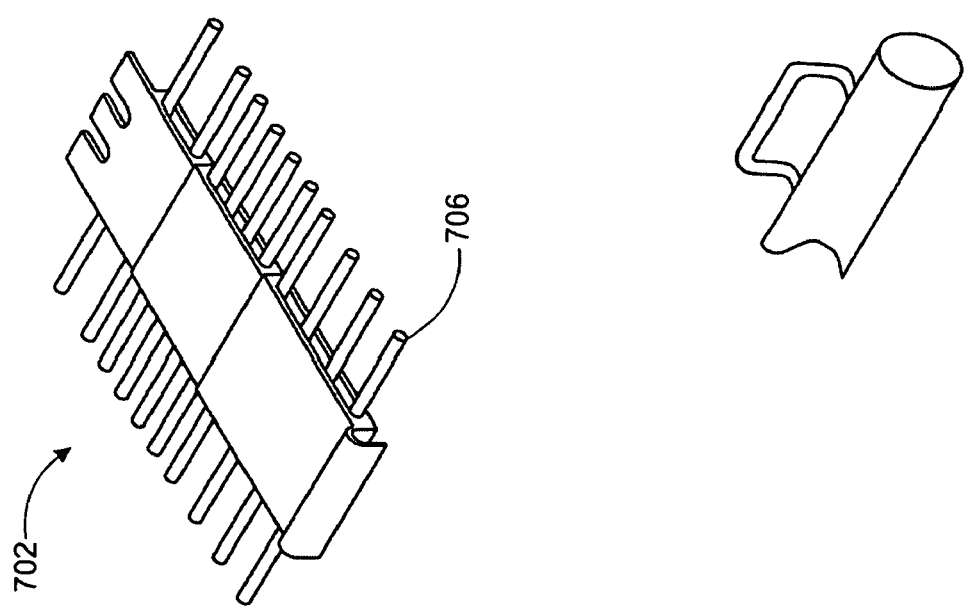
Figure 7B:
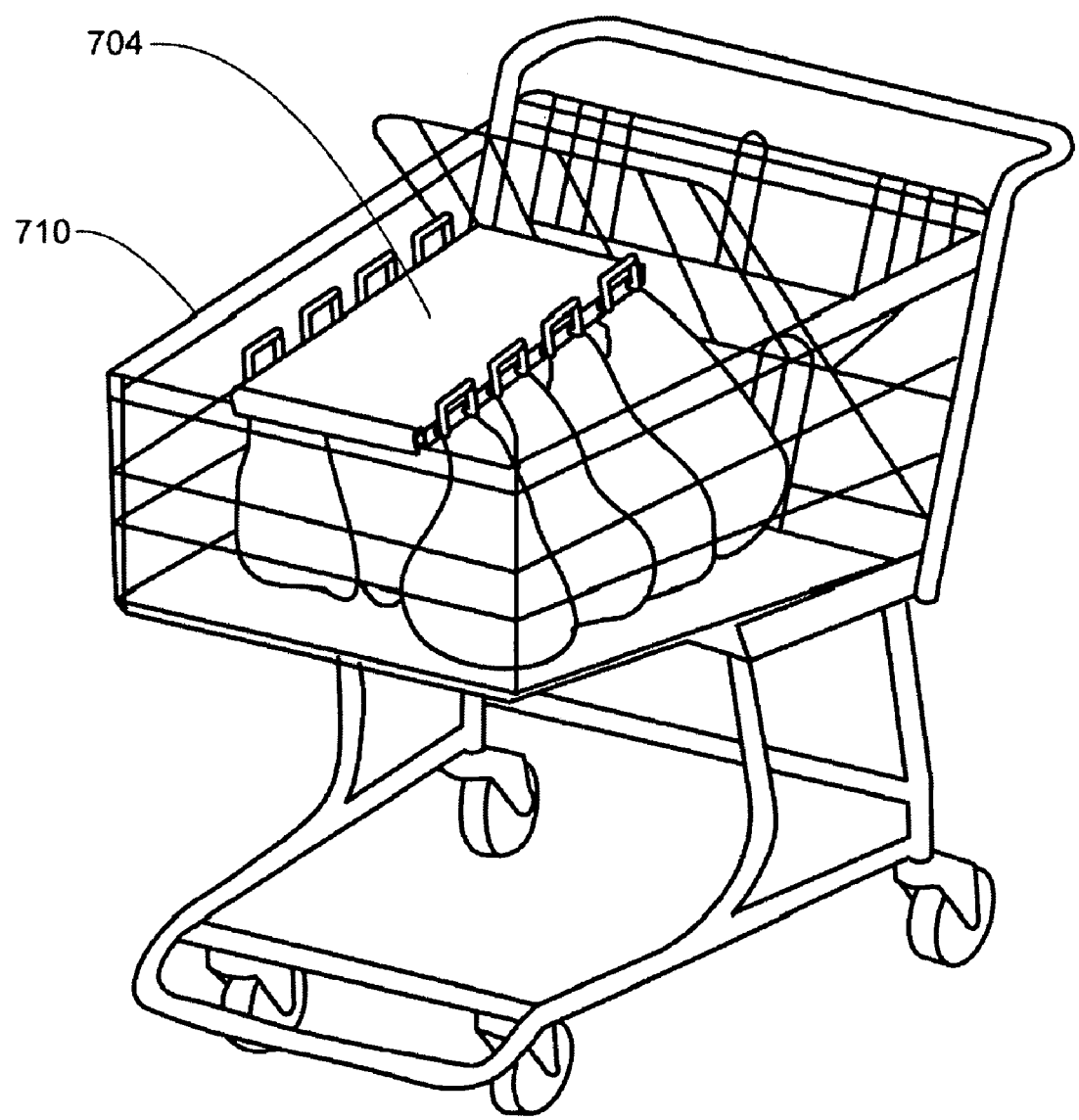
Figure 7C:
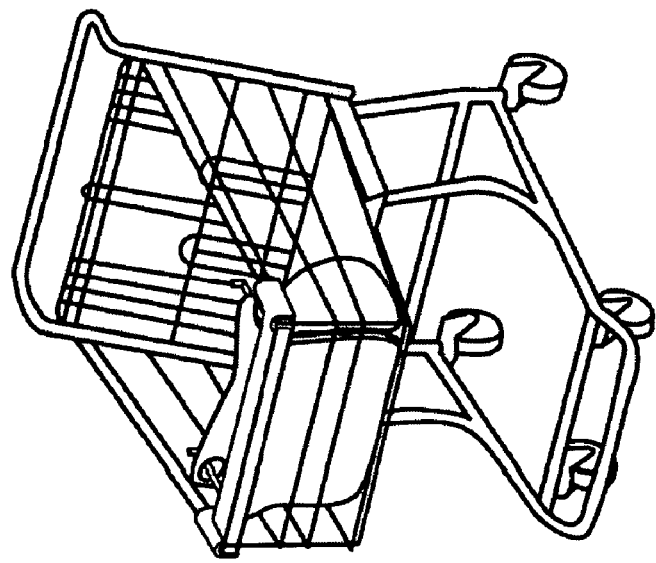
Figure 7C:
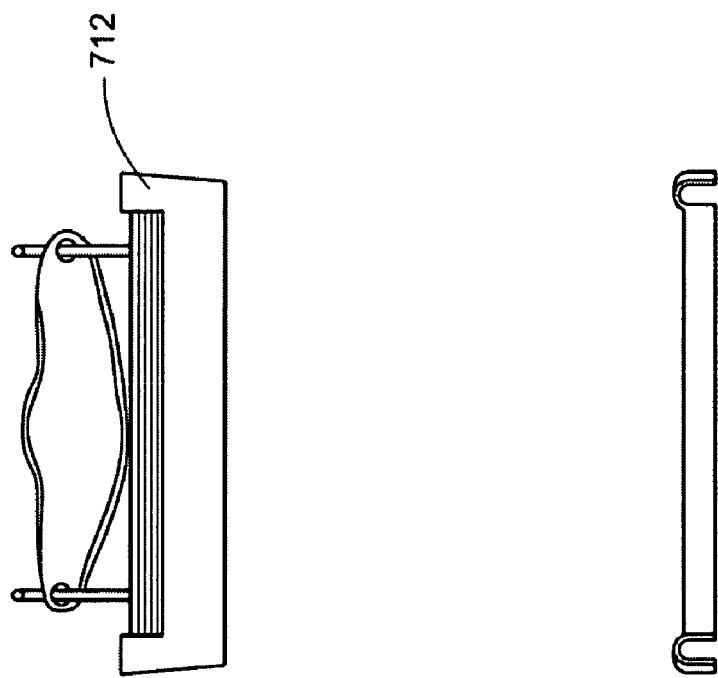

SHOPPING CART. Referring now to FIGS. 7A-7C various embodiments of a self-bagging shopping cart are shown. In one embodiment, the self-bagging apparatus is separate from the shopping cart. However, in other embodiments, the self-bagging apparatus is part of the shopping cart. Referring to FIG. 7A, an expandable embodiment of a bagging apparatus is shown 702, as well as a non-expandable embodiment 704. Both embodiments of the bagging apparatus 702, 704 include bag handles 706, 708 to hold the shopping bags. Referring to FIG. 7B, the bagging apparatus 704 is shown in a shopping cart 710.

Referring now to FIG. 7C, an alternate embodiment of the bagging apparatus is shown. In this embodiment, the bagging apparatus 712 accommodates a stack of bags. As the user requires another bag, the user pulls the next one from the stack. The bagging apparatus 712 is sized such that it hangs onto a standard shopping cart. In some embodiments, the bagging apparatus 712 may be permanently attached to the shopping cart, however, in other embodiments, the bagging apparatus is removable.

In all of the bagging apparatus shown in FIGS. 7A-7C, the apparatus may be made form plastic, metal or wood, and is sized/dimensioned for a particular shopping cart. Thus, depending o the size and shape of the shopping cart, the apparatus will be sized accordingly.

The self-bagging apparatus accommodates shopping bags. When the user takes an item off a store shelf or display, the user can directly place the item in the shopping bags themselves.

Figure 8:
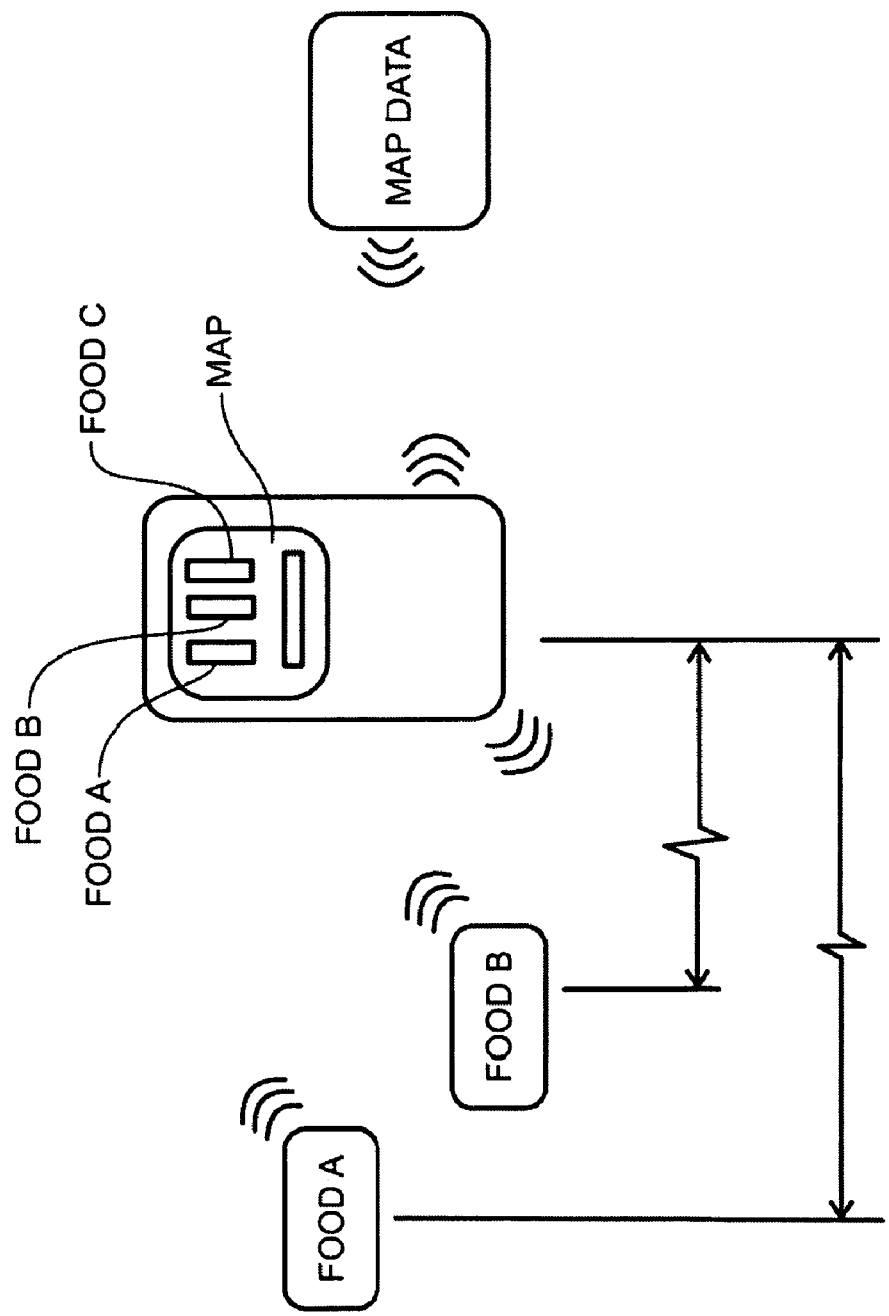
FIG. 8 is an illustrative view of one embodiment of the device communicating position, data for food items to the user.

SPEEDSHOPPER. One embodiment of the system is a speed-shopping system. The speed-shopping system is managed by the user profile. In the user profile, the user may make and save shopping lists. The system may suggest stores based on time of day desired, items desired, crowds, expected total shopping time. The user may select a store and the profile may additionally provide the user with a trip tick/map to the store which may include a suggested itinerary for more efficient shopping or to maintain cold items, etc. Additionally, in some embodiments, the device includes a GPS system. In this embodiment, the device may display a map of the store with locations of the items on the user's shopping list. Referring to FIG. 8, an illustration of this embodiment is shown.

Other embodiments include a vibrating shopping cart handle that may vibrate when the user comes within a predetermined proximity to an item on the shopping list. Other embodiments include an audio alarm and still other embodiments include a combination audio, vibrate and/or combination of visual and any other type of indication to the user.

In one embodiment, the speed-shopping system includes purchasing the food items or other products using the device. In still other embodiments, the device on the cart may track the addition of items into the shopping cart (either by user indication, scan, RFID transponder indication, or other) and tally the items. When the cart moves past a particular point in the store, for example, within 3 feet of the door, the device may charge the user's profile electronic account the total of the food items or other items that have been placed in the cart. In some embodiments, the user bags the items using an embodiment of the above described self-bagging apparatus (shown in FIGS. 7A-7C).

SMART SHELVES. Another embodiment includes a smart shelf system. In one embodiment, the shelves may include a means for signaling the device. The means can include, but is not limited to, one or more of the following: an electronic display on the store shelf, a light, an RFID or other transponder. The shelf is used to signal to the device. However, in other embodiments, the transponder is located within the packaging of the food item. In the smart shelf embodiment, one transponder is located on the shelf. The transponder communicates with the device regarding the product located in the particular shelf location.

In some embodiments of the smart shelf, a monitor is included, or the entire shelf is a monitor. The monitor may signal with an audio or visual alarm or other type of signal. The smart shelf may also track the number of products located in a particular shelf location. This may be used to manage inventory or food items. In still other embodiments, a single transponder for an entire store may be used to monitor the activity of inventory or food items on the shelves. This may be used by store management or by a vendor to monitor activity of a particular food item or other type of product.

In one embodiment, the smart shopping system includes carts as described above with devices on the carts, as well as smart shelves, self bagging and auto-charging. However, in other embodiments, only one or any combination of these embodiments are included in the system.

In one embodiment, the devices on the shopping cart, linked to a network, may track users' rate of shopping based on the shopping list in the user profiles. In this way, a store may track the progress of any shopping, can re-route shoppers in real-time by changing the trip tick and direction on the map, may also be used to direct the users to a check out counter to prevent long lines.

In one embodiment, the shopping cart includes an electronic display that may play commercials or educate the consumer regarding nutrition or specials in the store.

In one embodiment, once the user enters the store, based on the users shopping list, the device sends the deli, butcher, baker, florist, prescription, or any other customized order available in the store, electronically to the particular service area. Thus, the orders are placed and timed so that the items will be ready when the device directs the user to the area for the pick-up.

In some embodiments, the RFID transponder is on the food items. In some embodiments, the RFID transponder is on shelves. In some embodiments, the device reads bar codes on the food item with a camera. In other embodiments, the device reads the bar code with a bar code scanner. In some embodiments, the device contains a camera which physically recognizes product. Some embodiments include a web portal, where the user sets up ID, all rules and databases customized via web portal which is then downloadable onto the device. Some of these embodiments include a pay-for service.

INFORMATION AND DATABASES. The food item information is contained in a database. As described above, the database is either stored on the device and/or updated by an outside/remote database or may be stored on a remote database where the device accesses the remote database for all food item information. In some embodiments of the store embodiments as described above, a locally accessed database may be available and accessible to the device while in the store, i.e., in addition to the device's stored database, the store itself may "broadcast" a database. In any case, the device may access multiple databases. In some embodiments, the databases are multi-dimensional database. These allow searching through unstructured data or an expert/learned system. These databases also allow users to search by any attribute.

In some embodiments, the databases are built by the users, thus, as the user chooses a food item, the database adds the food item to the user's database, thus customizing the database through use. This is a learning database.

The communication between the database and the device may include any method of transferring information from one device to another. This includes, but is not limited to blue tooth, cellular communication, bar code, and radio.

In some embodiments, the database tracks the food items ingested by a particular user. The database may suggest food items based on an amount of time since the user ingested a particular item (according to their user profile or according to a store or organization broadcast message in the case of locally broadcast databases) for example, vegetables and fruits. The device may suggest the item either by audio, or visual, including but not limited to, a picture.

The following types of data may be included in the database(s). Various embodiments may be used alone or in any combination.

Nutritional Data. Nutritional data may be provided by existing databases. Additional or updated information for nutritional information may be downloaded from the web or purchased or otherwise provided by a company or organization.

Medical Data. Interaction data exists in a database in one embodiment. This can track allergies and reactive substances and advice user of same. Users may update their user profile and based on also, program products to be avoided based on medical data.

Third party rules. These can be parent rules, children rules managing elder parents, institutional/assisted living rules, or rules provided by a particular medical treatment group.

Self rules. These include warnings and others that are pre-programmed or otherwise set or selected by the user.

Group Sensitivities. This database information may include known sensitivities in the medical world. Advocacy groups may also publish suggested database information that may be downloaded or otherwise incorporated into a user profile.

Individual Sensitivities and Preferences. These can be ingredient or other based, user may program into the user profile or otherwise into the database.

Biometrics. These may include blood glucose readings, pulse and respiratory information and/or blood pressure. In some embodiments, the biometrics may be real-time.

Figure 10:
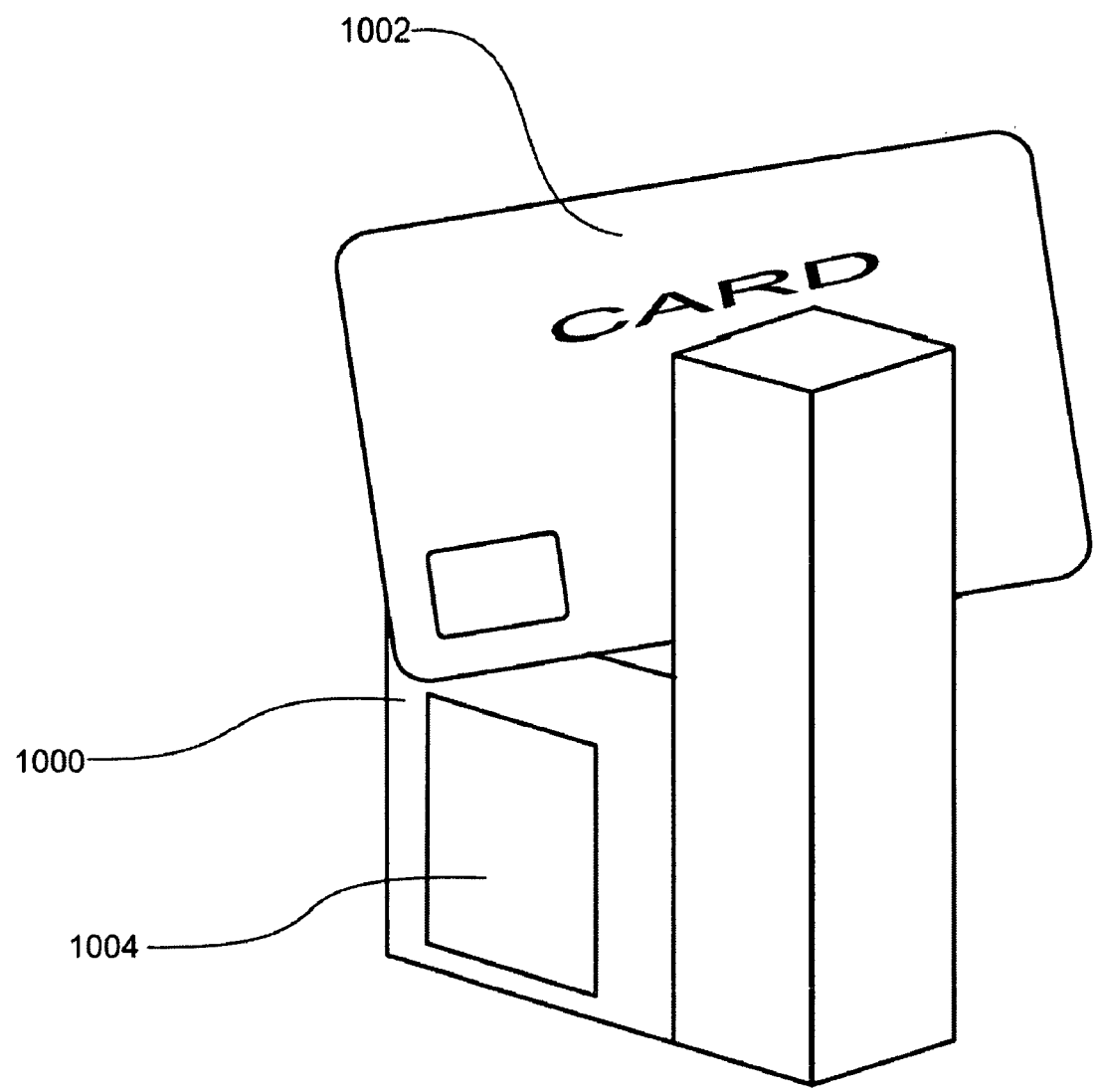
FIG. 10 is an illustrative view of one embodiment of a unit reader.
Figure 11:
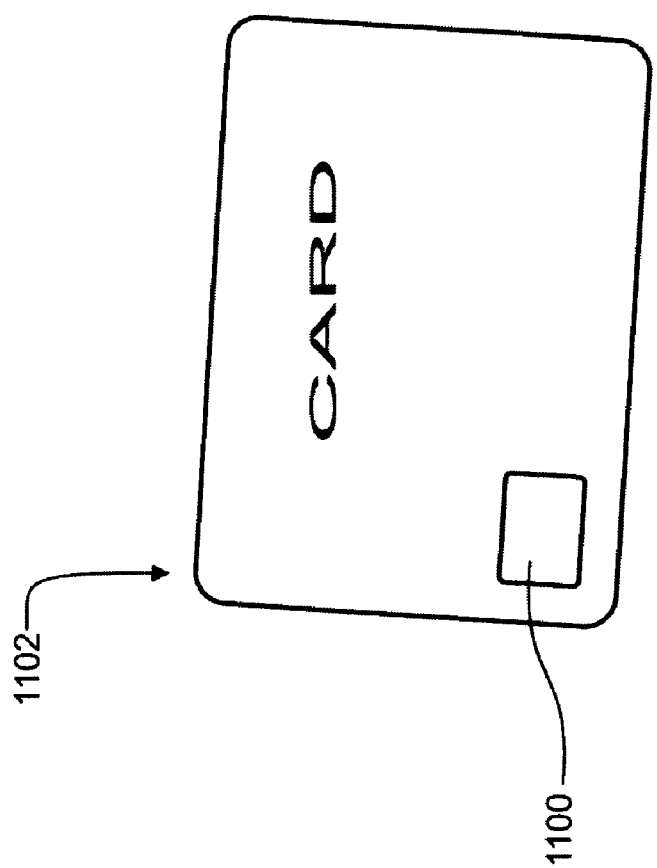
FIG. 11 is an illustrative view of one embodiment of a device incorporated onto a card.

Although various embodiments of the device and implementation of the food management methods have been described, additionally, the device may be a stand-alone device, or a magnetically readable strip on a card, for example, a user's credit card. Referring to FIG. 10, in a smart shopping embodiment, the user interacts with a unit 1000 on the shelf by sliding their card 1002 into the unit 1000. The unit 1000 reads the card and may display a message for the user on the unit display 1004. Referring to FIG. 1, the readable section 1100 may be embodied onto any type of card 1102.

Figure 12:
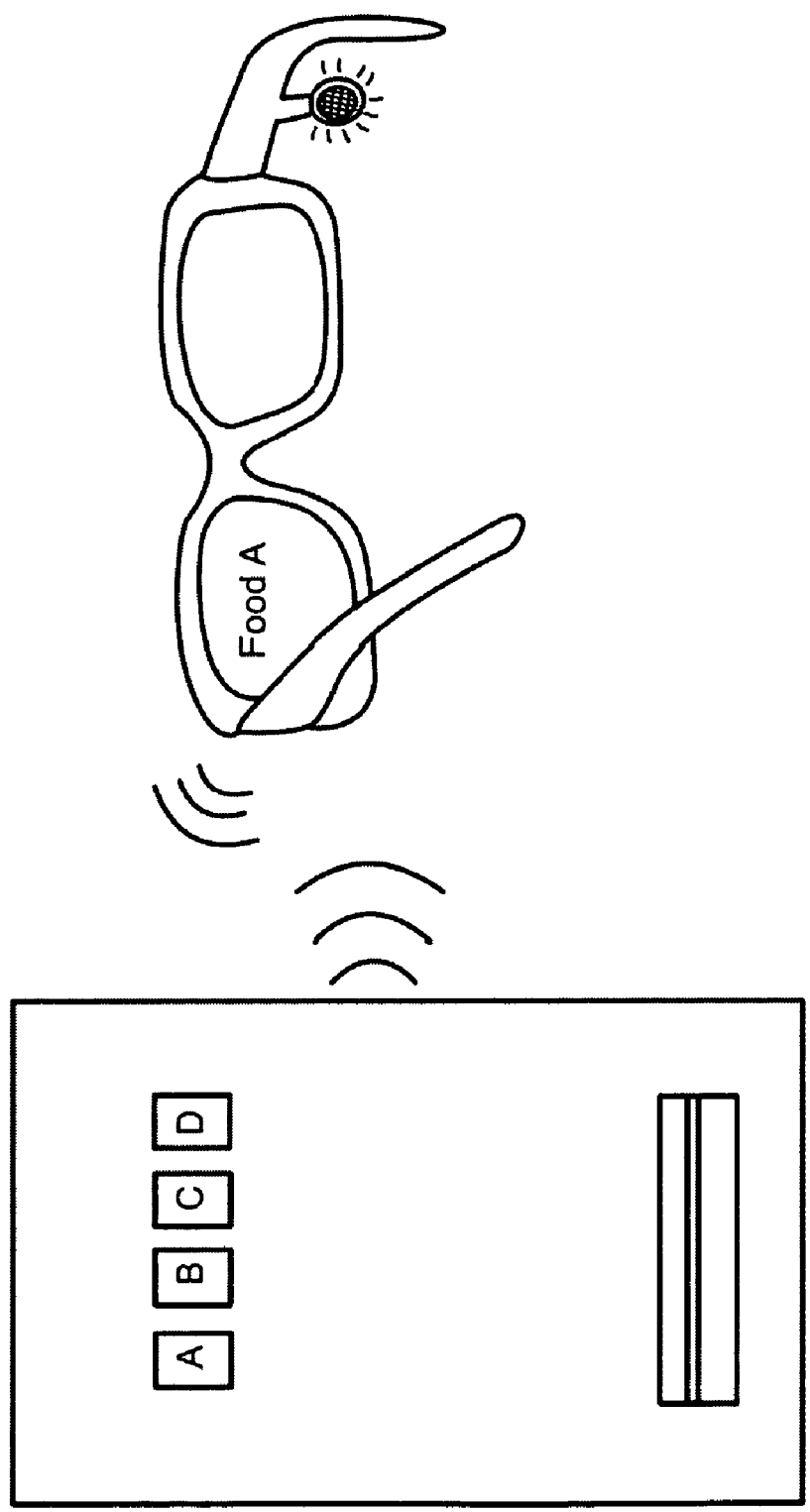
FIG. 12 is an illustrative view of one embodiment of a device being incorporated into glasses.

For various embodiments described herein, RFID may include an EPC Gen2: UPC label replacement. Vending machines may include RF communication. The device may include a GPS and/or internet connection. Stores can include WiFi. The device may be included on a pair of glasses (see FIG. 12), for example, and include a visual on the glasses for the user to view. The signal means may include an RFID, bar code, hex code (proprietary bar code/specialty bar code). Current standard RFID include 125 KHz (LF) low frequency-general carrier frequency, speed pass. The RFID in some embodiment may be long distance 13.56 Mhz. HF-high frequency, ISO 14443, ISO 15693, 900 MHz-UHF-EPC Gen2 (Electronic Product Code). Also, some embodiments include 2.4 GHz-WiFi tags. The RFID device may include read and write capabilities. Also, the RFID may include a permanent read only area with a unique serial number that can never be changed. Some of these tags may be set-up to be read-only, write once memory (used as a fuse). In other embodiments, the RFID tags may be WORM ("write once ready many"). In some embodiments, a store code can be imparted onto the product at the manufacturing facility.

Figure 9:
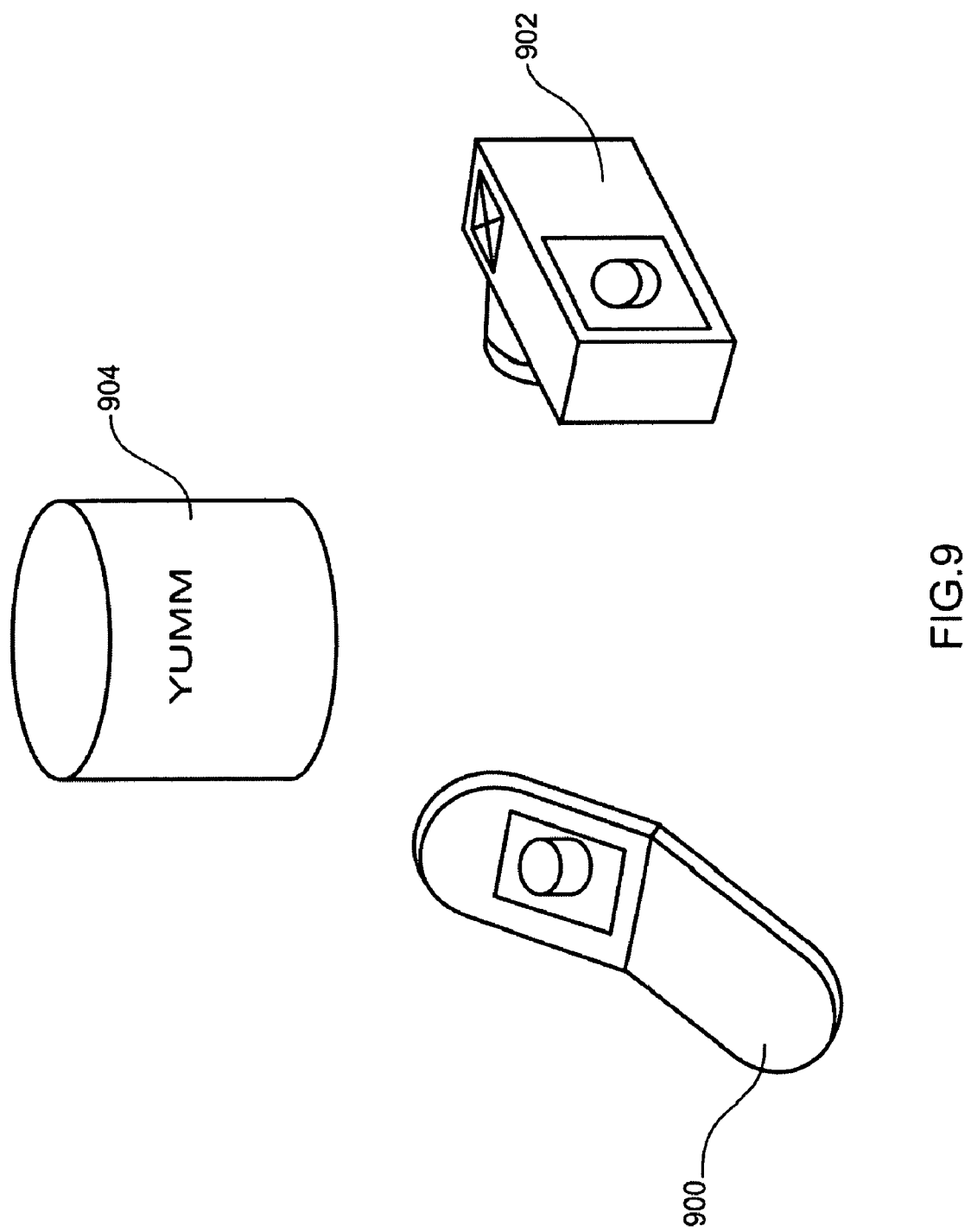
FIG. 9 is an illustrative view of various embodiments of food item image recognition embodiments.

In some embodiments, the food item is recognized optically with a camera (see FIG. 9). In some embodiments, a camera is on a cell phone 900 or other multi-functional device is used. In one embodiment, a stand-alone camera 902 may be the device. The optical recognition may be based on a picture of the whole product 904 or a picture of the label. In other embodiments, optical image recognition of UPC label, bag or product itself is used.

In still other embodiments, the food item identity may be determined by a chart/flip chart/booklet including the food items along with a code. In these embodiment, the user either manually enters this code or there is a bar code to scan into the device.

Nutritional information may include, but is not limited to, calories, serving size, glycemic index, fat content, cholesterol content, saturated fat content, fiber content, sodium, presence of particular amino acids, percentage daily allowance of vitamins, percentage of daily allowance of any nutrient, percentage daily allowance of calories, fat, and/or cholesterol, allergy items included in the food item, and known interactions with medications.

In some embodiments, the device may give a shock to the user when the user selects or eats a food item in which they chose to setup a rule against eating or purchasing. In other embodiments, the device may suggest a wine pairing based on criteria to complement a food item or food items or recipe. In some embodiments, recipes are available on the database and automatically include items in the shopping list on the user profile, if desired.

The smart-shelf may be implemented using IR or RF or any wireless protocol known to one of ordinary skill in the art. The shelf may include an LCD display. The shelf may be designed as a low voltage system for low power requirements. In some embodiments, the shelf may be implemented with a 2 way radio (or IR communication), memory, and software, indicator, power source (solar powered) or connected to a power source, may include an LCD, or may include only a LED or light. In some embodiments, the shelf may be capacitor charged either by solar or electric source. The shelf may, in some embodiments, include a battery onboard, and in some embodiment, the battery may be rechargeable.

While the principles of the invention have been described herein, it is to be understood by those skilled in the art that this description is made only by way of example and not as a limitation as to the scope of the invention. Other embodiments are contemplated within the scope of the present invention in addition to the exemplary embodiments shown and described herein. Modifications and substitutions by one of ordinary skill in the art are considered to be within the scope of the present invention.

What is claimed is:

1. A medical device comprising:
    an RFID reader for receiving information from at least one RFID transponder;
    a memory for storing a database; and
    at least one processor for processing information, wherein said medical device is a remote controller for a second medical device.

2. The medical device of claim 1 wherein said medical device is an infusion device.

3. The medical device of claim 1 wherein said medical device is a glucose monitoring device.

4. The medical device of claim 1 wherein said database includes user profile information.

5. The medical device of claim 1 wherein said database includes information relating to food.

6. The medical device of claim 1 wherein said database is a learning database.

7. The medical device of claim 1 further comprising a display for displaying at least a portion of said information.

8. A method for use in a medical device the method comprising:
   receiving information from an RFID transponder related to food;
   processing said information by comparing said information to a database;
   determining acceptability of said food;
   inputting an estimate of amount of said food item to be ingested by the body of the user;
   calculating estimated bolus amount of insulin required by the body of the user based upon at least one blood glucose value; and
   providing information related to acceptability to the user.

9. The method of claim 8 wherein said processing further comprising comparing said information to a food item and user profile database.

10. The method of claim 8 further comprising calculating a recommended amount of said food for user to ingest based on at least one blood glucose value.

11. The method of claim 8 further comprising:
    inputting at least one blood glucose value; and
    calculating recommended amount of said food item for user to ingest based at least upon said at least one blood glucose value.

12. The method of claim 8 further comprising:
    inputting an estimate of amount of said food item to be ingested by the body of the user; and
    calculating total caloric intake by user based on a sum of said inputs during a period of time.

13. A method for use in a medical device the method comprising:
    receiving information from an RFID transponder related to food;
    processing said information by comparing said information to a database;
    determining acceptability of said food;
    inputting at least one blood glucose value;
    calculating recommended amount of said food item for user to ingest based at least upon said at least one blood glucose value; and
    providing information related to acceptability to the user.

14. The method of claim 13 wherein said processing further comprising comparing said information to a food item and user profile database.

15. The method of claim 13 further comprising calculating a recommended amount of said food for user to ingest based on at least one blood glucose value.

16. The method of claim 13 further comprising:
    inputting an estimate of amount of said food item to be ingested by the body of the user; and
    calculating estimated bolus amount of insulin required by the body of the user based upon at least one blood glucose value.

17. The method of claim 13 further comprising:
    inputting an estimate of amount of said food item to be ingested by the body of the user; and
    calculating total caloric intake by user based on a sum of said inputs during a period of time.

* * * * *